(12) United States Patent
Milliman et al.

(10) Patent No.: US 6,330,965 B1
(45) Date of Patent: Dec. 18, 2001

(54) SURGICAL STAPLING APPARATUS

(75) Inventors: Keith L. Milliman, Bethel; Frank J. Viola, Sandy Hook; Joseph Orban, III, Norwalk; Randolph F. Lehn, Stratford, all of CT (US)

(73) Assignee: United States Surgical Corporation, Norwalk, CT (US)

( * ) Notice: Subject to any disclaimer, the term of this patent is extended or adjusted under 35 U.S.C. 154(b) by 0 days.

(21) Appl. No.: 09/680,093

(22) Filed: Oct. 5, 2000

Related U.S. Application Data

(62) Division of application No. 09/166,378, filed on Oct. 5, 1998, now Pat. No. 6,079,606, which is a division of application No. 08/935,980, filed on Sep. 23, 1997, now Pat. No. 5,865,361.

(51) Int. Cl.⁷ .................................................. A61B 17/068
(52) U.S. Cl. ..................... 227/176.1; 227/19; 227/178.1
(58) Field of Search ................... 227/19, 175.1, 227/176.1, 178.1, 175.3

(56) References Cited

U.S. PATENT DOCUMENTS

| | | |
|---|---|---|
| Re. 34,519 | 1/1994 | Fox et al. . |
| 3,079,606 | 3/1963 | Bobrov et al. . |
| 3,490,675 | 1/1970 | Green et al. . |
| 4,244,372 | 1/1981 | Kapitanov et al. . |
| 4,429,695 | 2/1984 | Green . |
| 4,520,817 | 6/1985 | Green . |
| 4,589,413 | 5/1986 | Malyshev et al. . |
| 4,605,001 | 8/1986 | Rothfuss et al. . |
| 4,608,981 | 9/1986 | Rothfuss et al. . |
| 4,610,383 | 9/1986 | Rothfuss et al. . |
| 4,633,861 | 1/1987 | Chow et al. . |
| 4,633,874 | 1/1987 | Chow et al. . |
| 4,672,964 | 6/1987 | Dee et al. . |
| 4,763,669 | 8/1988 | Jaeger . |
| 4,863,088 | 9/1989 | Redmond et al. . |
| 4,880,015 | 11/1989 | Nierman . |
| 4,892,244 | 1/1990 | Fox et al. . |
| 4,978,049 | 12/1990 | Green . |
| 4,991,764 | 2/1991 | Mericle . |
| 5,040,715 | 8/1991 | Green et al. . |
| 5,065,929 | 11/1991 | Schulze et al. . |
| 5,071,052 | 12/1991 | Rodak et al. . |
| 5,074,454 | 12/1991 | Peters . |
| 5,083,695 | 1/1992 | Foslien et al. . |
| 5,111,987 | 5/1992 | Moeinzadeh et al. . |
| 5,129,570 | 7/1992 | Schulze et al. . |
| 5,141,144 | 8/1992 | Foslien et al. . |
| 5,152,279 | 10/1992 | Wilk . |
| 5,209,747 | 5/1993 | Knoepfler . |
| 5,275,608 | 1/1994 | Forman et al. . |
| 5,282,826 | 2/1994 | Quadri . |
| 5,307,976 | 5/1994 | Olson et al. . |
| 5,312,023 | 5/1994 | Green et al. . |
| 5,318,221 | 6/1994 | Green et al. . |
| 5,326,013 | 7/1994 | Green et al. . |
| 5,330,502 | 7/1994 | Hassler et al. . |

(List continued on next page.)

FOREIGN PATENT DOCUMENTS

| | | |
|---|---|---|
| 4300307 | 7/1994 | (DE) . |
| 0484677 | 5/1992 | (EP) . |
| 0589306 | 3/1994 | (EP) . |
| 0591946 | 4/1994 | (EP) . |
| 0592243 | 4/1994 | (EP) . |
| 0621009 | 10/1994 | (EP) . |
| 0656188 | 6/1995 | (EP) . |
| 2681775 | 10/1991 | (FR) . |
| 980703 | 12/1982 | (SU) . |
| 990220 | 1/1983 | (SU) . |

*Primary Examiner*—Scott A. Smith

(57) ABSTRACT

A surgical stapling device particularly suited for endoscopic procedures is described. The device can be used with both articulating and non-articulating disposable loading units and has a sensing mechanism for sensing the type of disposable loading unit secured to the device.

9 Claims, 39 Drawing Sheets

U.S. PATENT DOCUMENTS

| | | |
|---|---|---|
| 5,332,142 | 7/1994 | Robinson et al. . |
| 5,350,391 | 9/1994 | Iacovelli . |
| 5,354,311 | 10/1994 | Kambin et al. . |
| 5,374,277 | 12/1994 | Hassler . |
| 5,376,095 | 12/1994 | Ortiz . |
| 5,383,888 | 1/1995 | Zvenyatsky et al. . |
| 5,397,046 | 3/1995 | Savage et al. . |
| 5,415,334 | 5/1995 | Williamson, IV et al. . |
| 5,415,335 | 5/1995 | Knodel, Jr. . |
| 5,433,721 | 7/1995 | Hooven et al. . |
| 5,465,895 | 11/1995 | Knodel et al. . |
| 5,467,911 | 11/1995 | Tsuruta et al. . |
| 5,474,566 | 12/1995 | Alesi et al. . |
| 5,474,571 | 12/1995 | Lang . |
| 5,484,451 | 1/1996 | Akopov et al. . |
| 5,486,185 | 1/1996 | Freitas et al. . |
| 5,487,500 | 1/1996 | Knodel et al. . |
| 5,507,426 | 4/1996 | Young et al. . |
| 5,535,935 | 7/1996 | Vidal et al. . |
| 5,582,617 | 12/1996 | Klieman et al. . |
| 5,605,272 | 2/1997 | Witt et al. . |
| 5,630,539 | 5/1997 | Plyley et al. . |
| 5,762,255 | 6/1998 | Chrisman et al. . |
| 5,797,537 | 8/1998 | Oberlin et al. . |
| 5,820,009 | 10/1998 | Melling et al. . |
| 5,855,311 * | 1/1999 | Hamblin et al. .................. 227/176.1 |
| 6,010,054 * | 1/2000 | Johnson et al. ........................ 227/19 |
| 6,032,849 * | 3/2000 | Mastri et al. ..................... 227/178.1 |
| 6,109,500 * | 8/2000 | Alli et al. ......................... 227/176.1 |

* cited by examiner

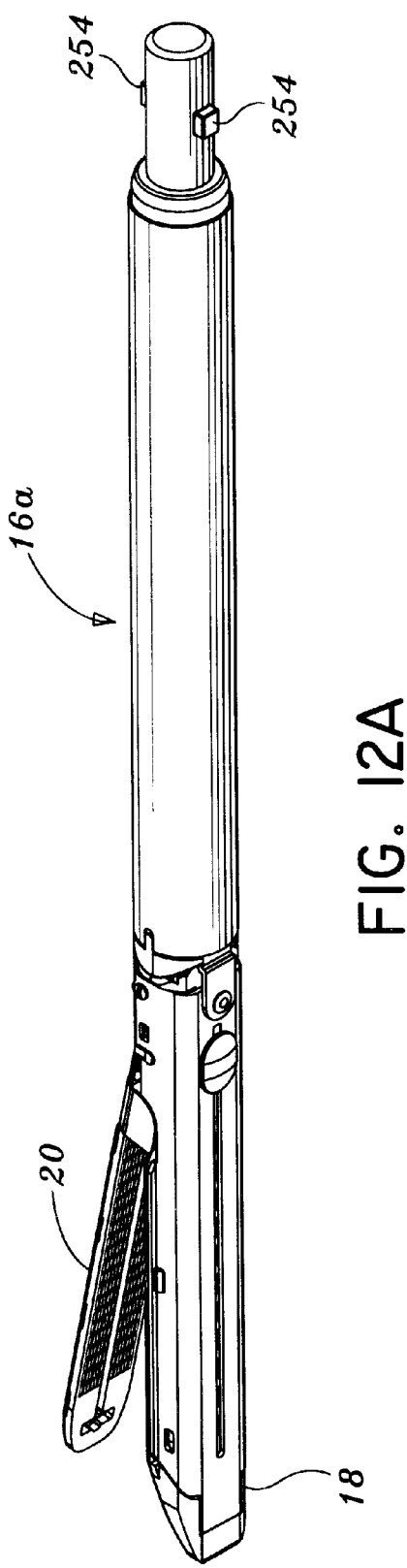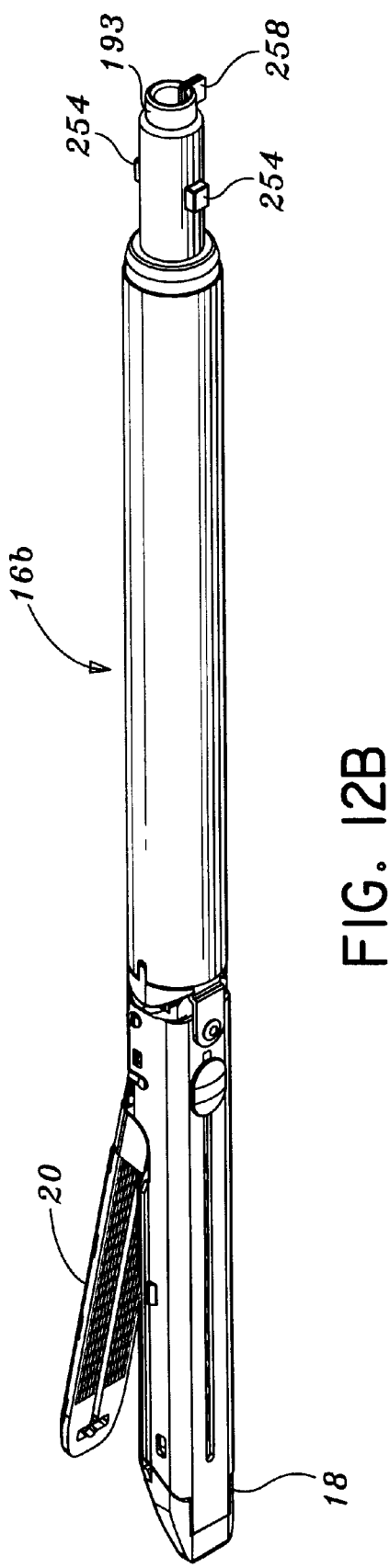
FIG. 12A
FIG. 12B

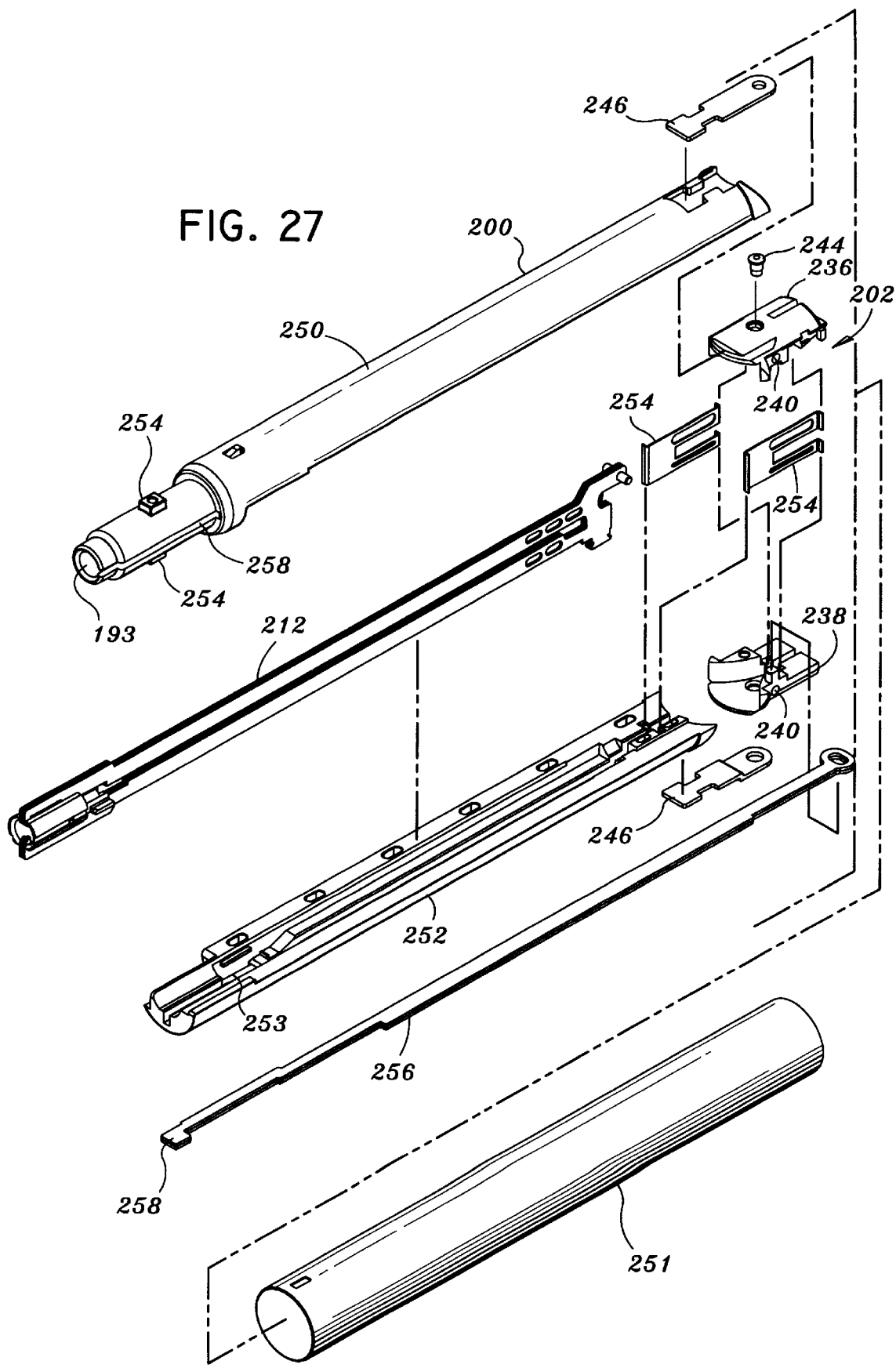

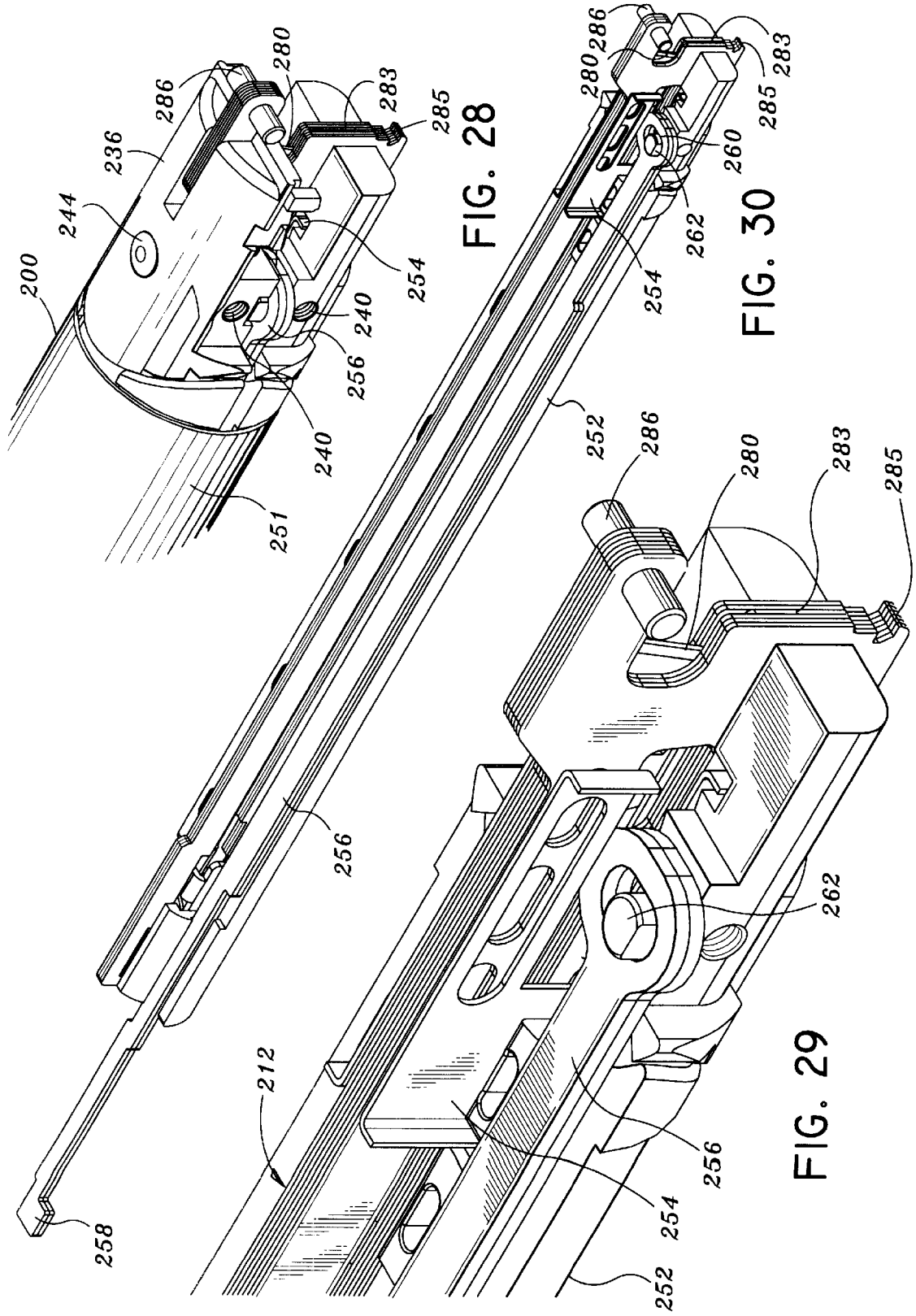

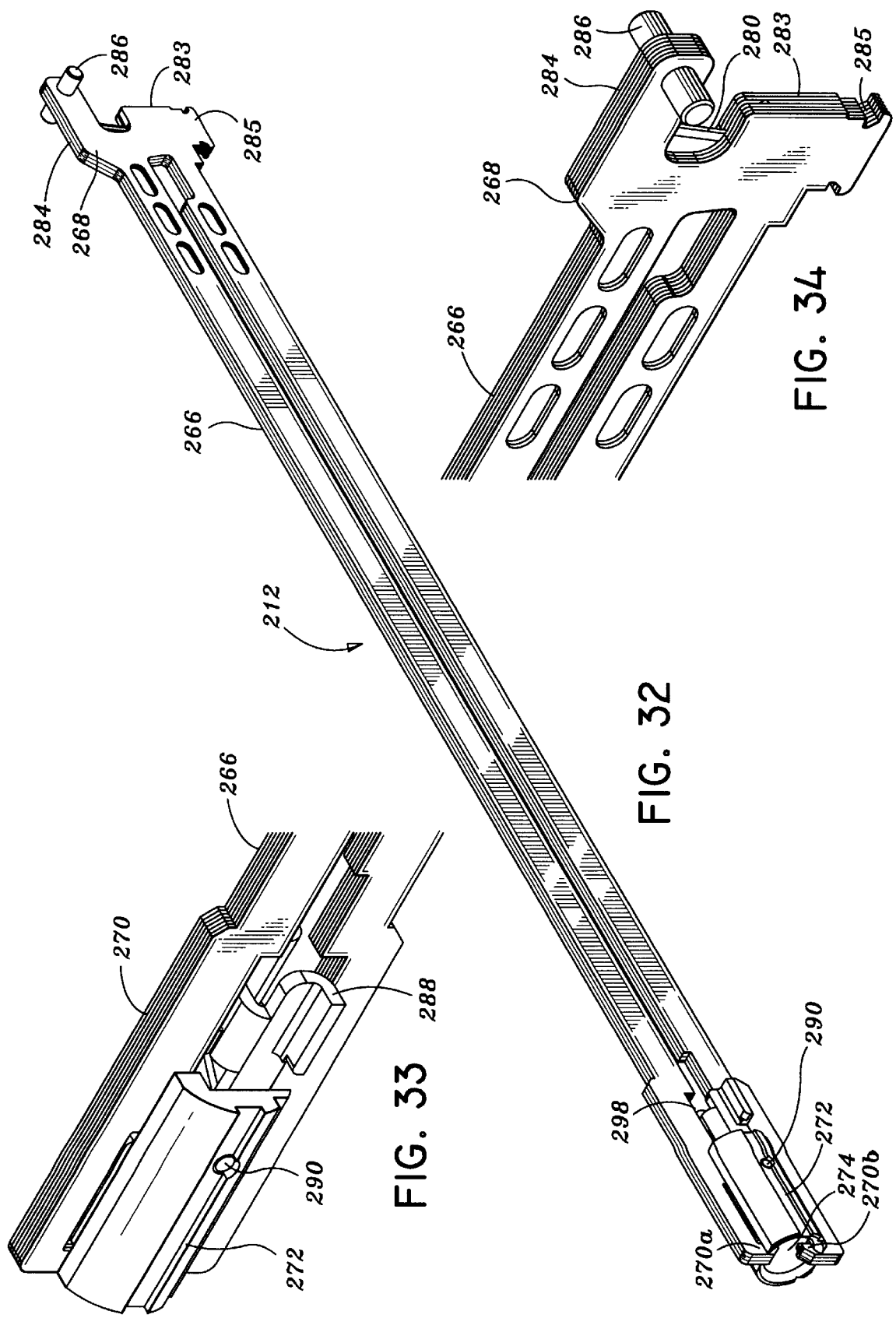

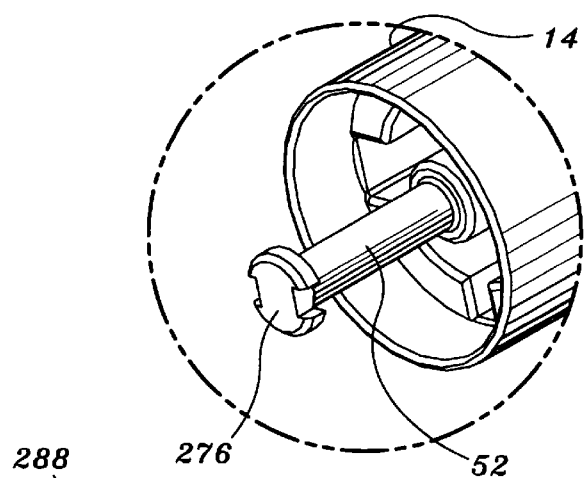
FIG. 35
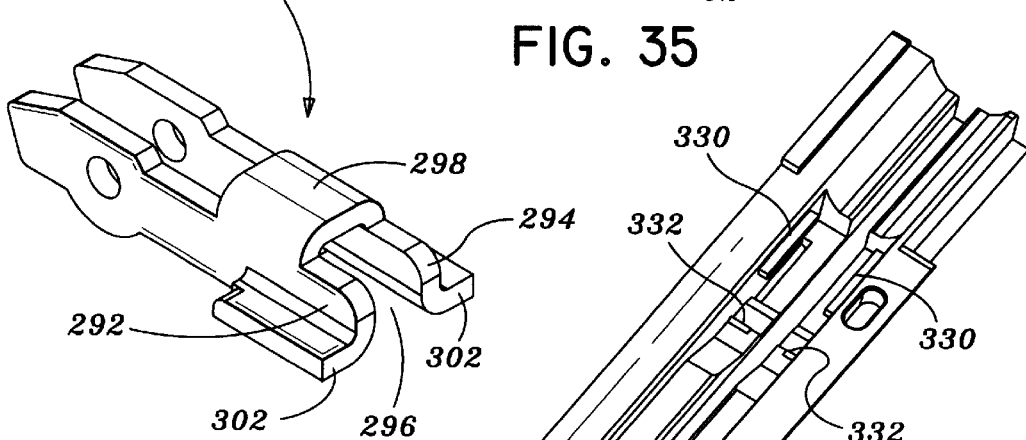
FIG. 36
FIG. 37
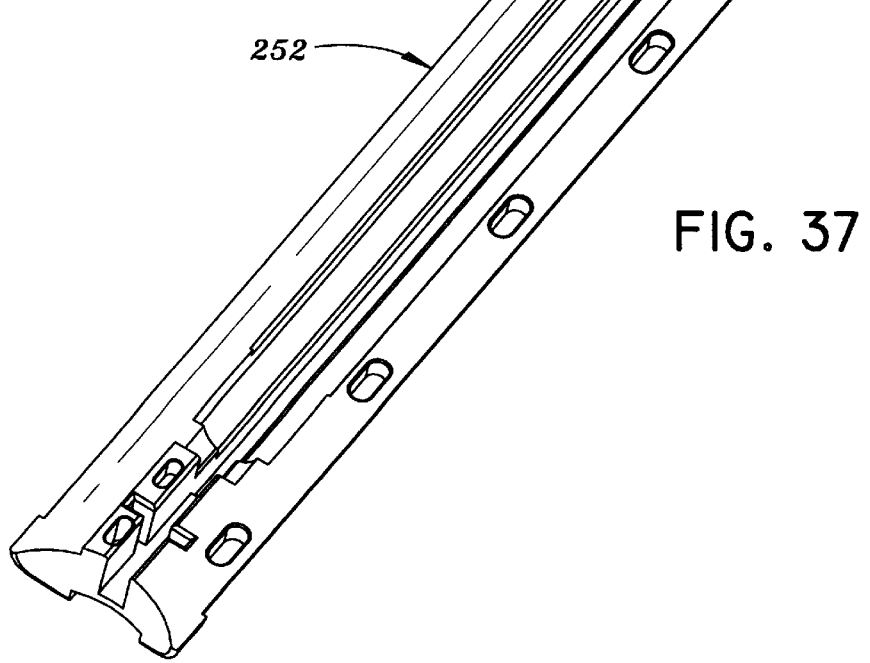

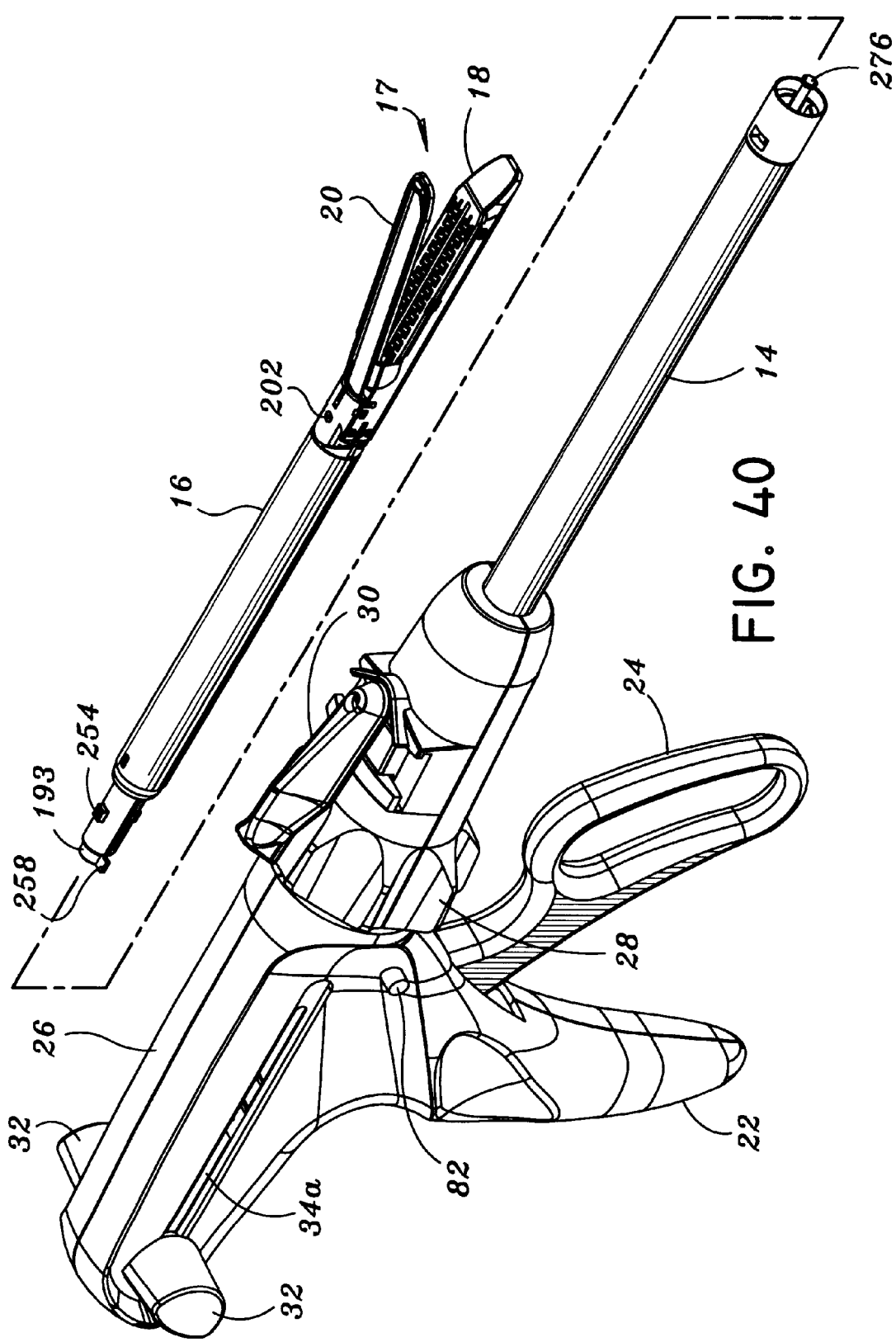

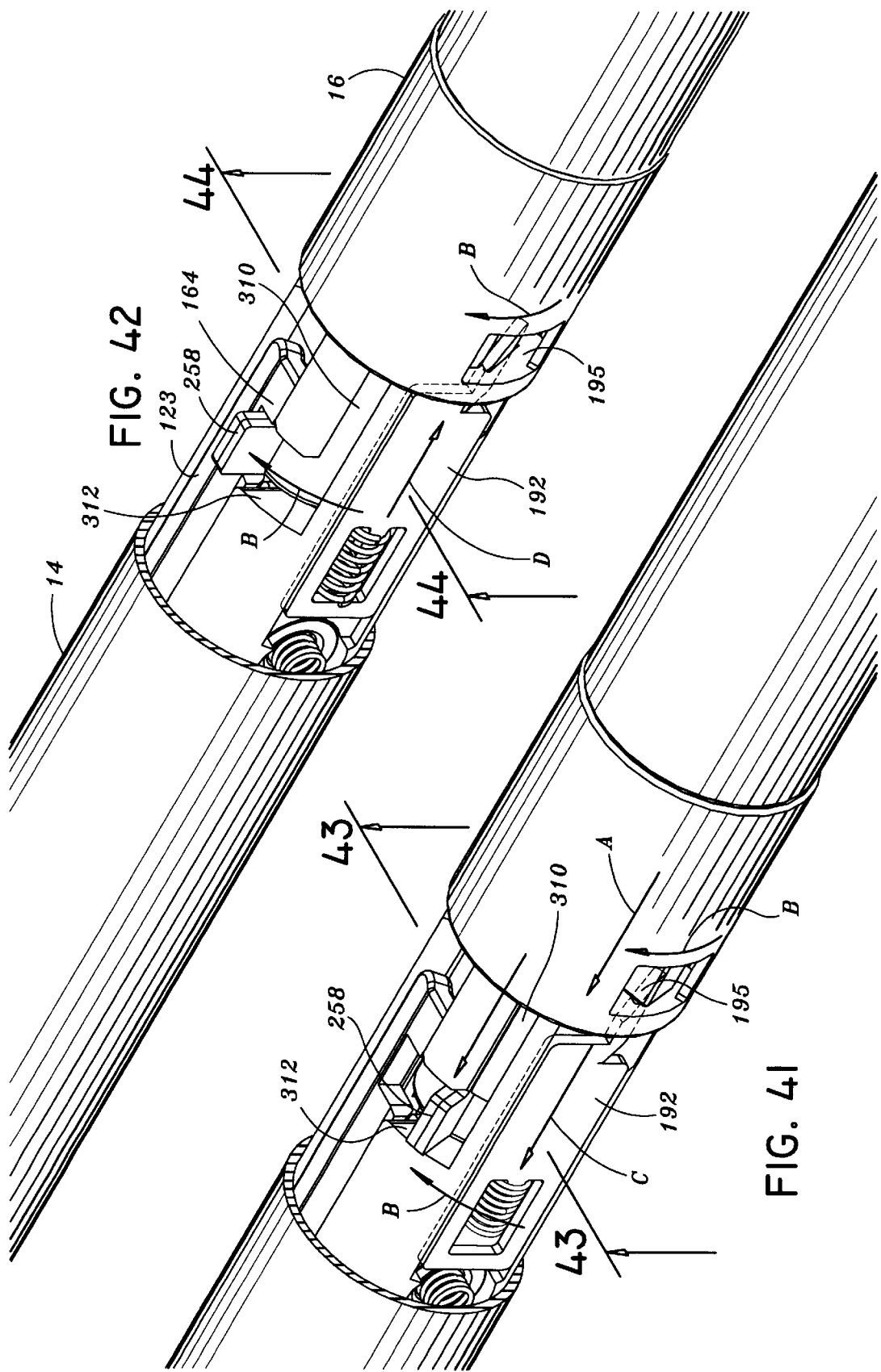

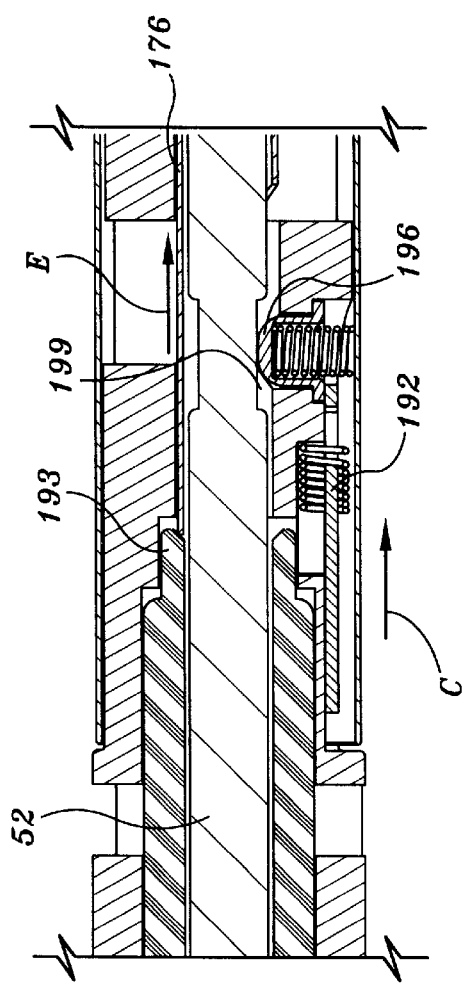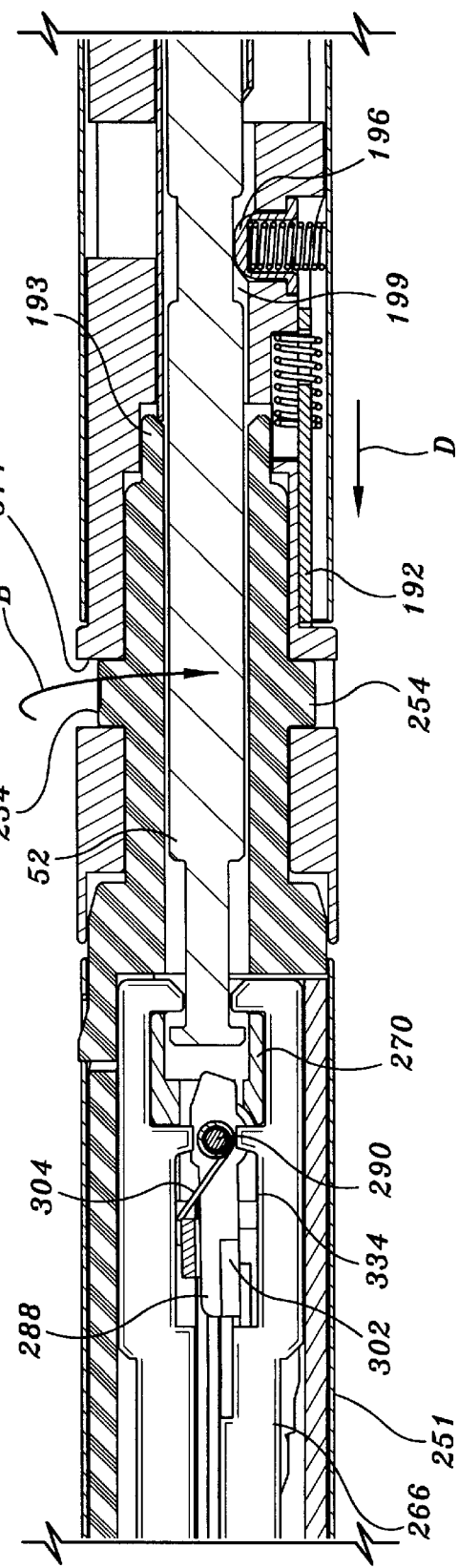

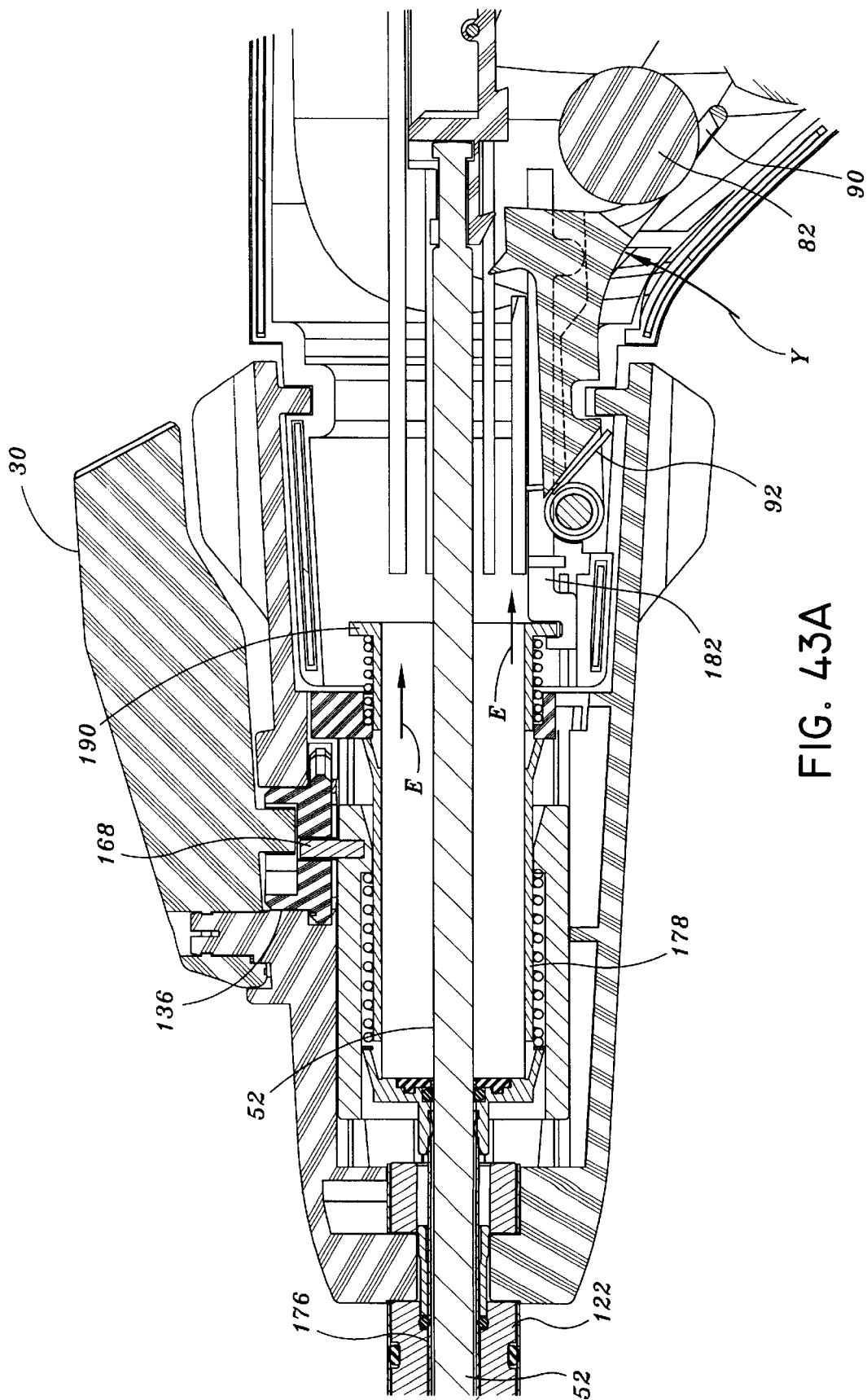

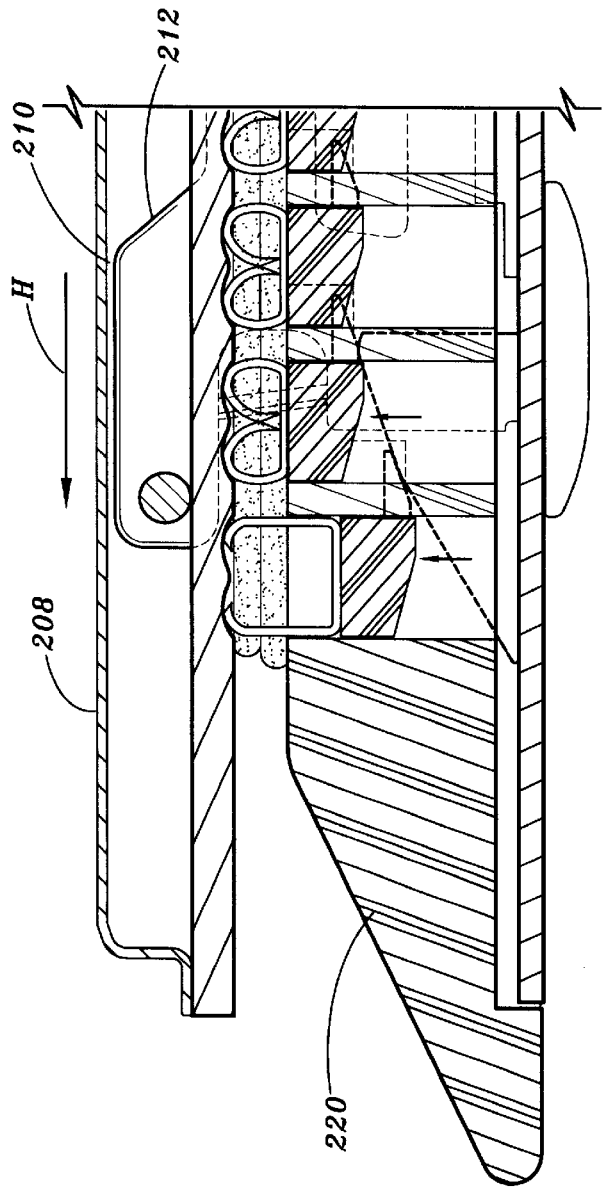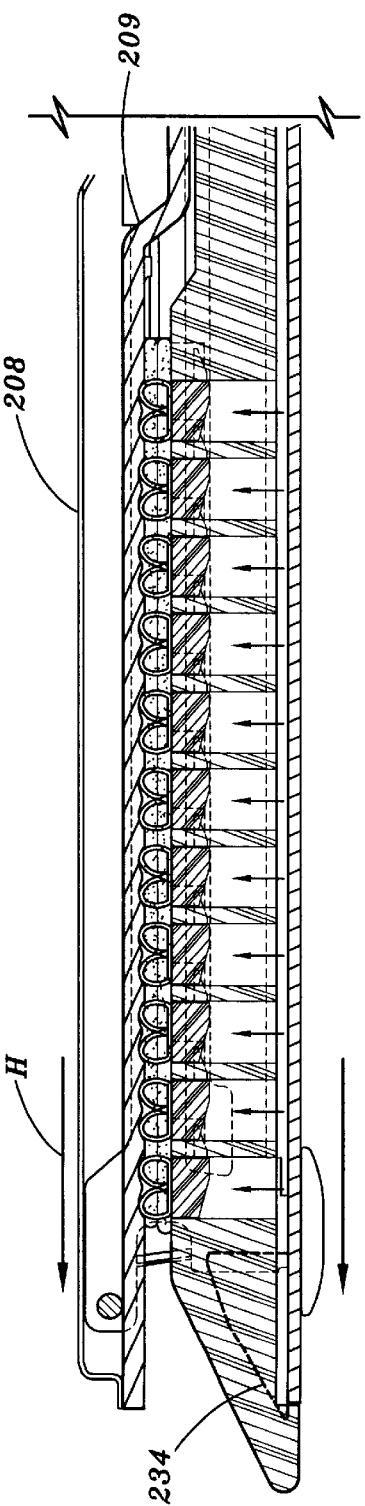
FIG. 51
FIG. 52

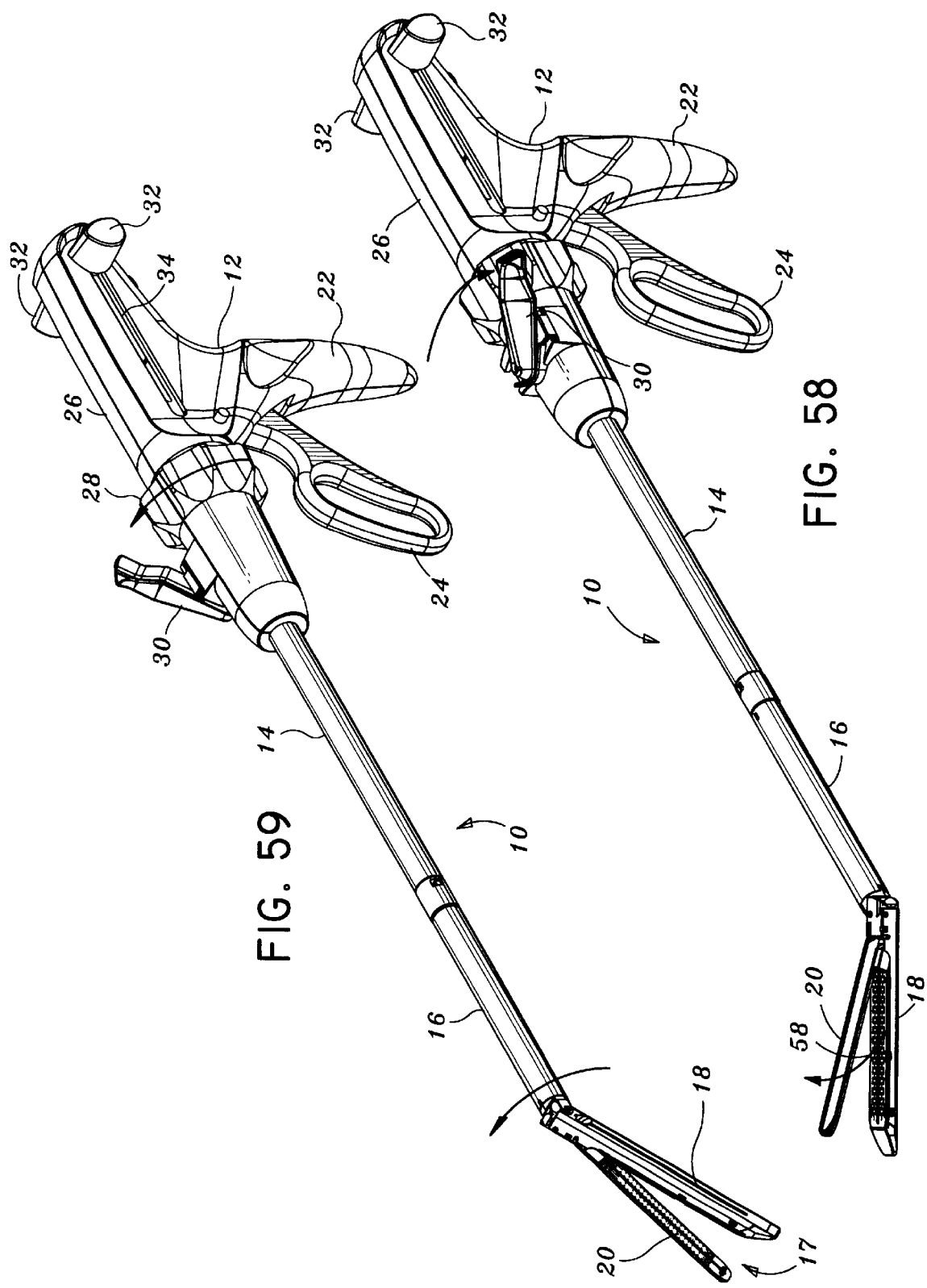

SURGICAL STAPLING APPARATUS

CROSS-REFERENCE TO RELATED APPLICATIONS

This application is a divisional of U.S. patent application Ser. No. 09/166,378, filed Oct. 5, 1998, now U.S. Pat. No. 6,079,606, which is a divisional of U.S. patent application Ser. No. 08/935,980, filed Sep. 23, 1997, now U.S. Pat. No. 5,865,361. Both are incorporated herein by reference.

BACKGROUND

1. Technical Field

This application relates to a surgical stapling apparatus, and more particularly, to an articulating mechanism for use with an endoscopic surgical stapling apparatus for sequentially applying a plurality of surgical fasteners to body tissue and optionally incising fastened tissue.

2. Background of Related Art

Surgical devices wherein tissue is first grasped or clamped between opposing jaw structure and then joined by surgical fasteners are well known in the art. In some instruments a knife is provided to cut the tissue which has been joined by the fasteners. The fasteners are typically in the form of surgical staples but two part polymeric fasteners can also be utilized.

Instruments for this purpose can include two elongated members which are respectively used to capture or clamp tissue. Typically, one of the members carries a staple cartridge which houses a plurality of staples arranged in at least two lateral rows while the other member has an anvil that defines a surface for forming the staple legs as the staples are driven from the staple cartridge. Generally, the stapling operation is effected by cam bars that travel longitudinally through the staple cartridge, with the cam bars acting upon staple pushers to sequentially eject the staples from the staple cartridge. A knife can travel between the staple rows to longitudinally cut and/or open the stapled tissue between the rows of staples. Such instruments are disclosed, for example, in U.S. Pat. Nos. 3,079,606 and 3,490,675.

A later stapler disclosed in U.S. Pat. No. 3,499,591 applies a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. Other examples of such staplers are disclosed in U.S. Pat. Nos. 4,429,695 and 5,065,929.

Each of the instruments described above were designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. No. 5,040,715 (Green, et al.); U.S. Pat. No. 5,307,976 (Olson, et al.); U.S. Pat. No. 5,312,023 (Green, et al.); U.S. Pat. No. 5,318,221 (Green, et al.); U.S. Pat. No. 5,326,013 (Green, et al.); and U.S. Pat. No. 5,332,142 (Robinson, et al.).

U.S. Surgical, the assignee of the present application, has manufactured and marketed endoscopic stapling instruments, such as the Multifire ENDO GIA* 30 and Multifire ENDO GIA* 60 instruments, for several years. These instruments have provided significant clinical benefits. Nonetheless, improvements are possible, for example, by reducing the cost and complexity of manufacture.

Current laparoscopic linear stapling devices are configured to operate with disposable loading units (U.S. Surgical) and staple cartridges (Ethicon) of only one size. For example, individual linear staplers are presently available for applying parallel rows of staples measuring 30 mm, 45 mm and 60 mm in length. Thus, during a normal operation, a surgeon may be required to utilize several different stapling instruments to perform a single laparoscopic surgical procedure. Such practices increase the time, complexity and overall costs associated with laparoscopic surgical procedures. In addition, costs are greater in designing and manufacturing multiple stapler sizes, as opposed to creating a single, multipurpose stapler.

It would be extremely beneficial to provide a surgical device for use during laparoscopic and/or endoscopic surgical procedures that can be employed with several different sized disposable loading units to reduce the overall costs associated with such procedures. It would also be particularly beneficial if the device could perform multiple tasks, using disposable loading units of varying size and of varying purpose, such as, for example, to staple, clip, cut and/or articulate.

In making improvements or modifications to the current instruments, it would be highly desirable not to sacrifice any of the important benefits of the MULTIFIRE ENDO GIA* 30 and 60 instruments as compared to other commercially available products, e.g., the endoscopic stapling instruments manufactured and marketed by Ethicon, Inc. For example, any improvement should advantageously provide a fresh knife blade for each firing of the instrument and ensure that the disposable loading unit is securely retained in the stapling instrument unless and until the operating team chooses to remove it. These advantages have historically been found in the U.S. Surgical instruments, but not in the Ethicon instruments.

SUMMARY

In accordance with the present disclosure, a surgical stapling apparatus for sequentially applying a plurality of fasteners to body tissue and simultaneously incising tissue is provided. The surgical stapling apparatus is adapted to receive disposable loading units having rows of staples having a linear length of between 30 mm and 60 mm. The surgical stapling apparatus is also adapted to receive articulating and non-articulating disposable loading units.

The surgical stapling apparatus includes a handle assembly having a movable handle and a stationary handle. The movable handle is movable through an actuation stroke to clamp tissue and to effect ejection of staples from the disposable loading unit. An elongated body extends distally from the handle assembly and defines a longitudinal axis. An actuation shaft having a toothed rack is operably associated with the movable handle by a pawl mechanism. The distal end of the actuation shaft is connected to a control rod having a distal end adapted to operatively engage an axial drive assembly located within a disposable loading unit.

The stapling apparatus includes an articulation mechanism having an articulation lever operatively engaged with a cam member having a stepped camming channel. The cam member is engaged with a translation member which includes a pin dimensioned to be received within the stepped camming channel such that pivotable movement of the lever causes linear movement of the translation member. A first articulation link includes a proximal end adapted to engage the translation member and a distal end adapted to engage a second articulation link positioned within the disposable loading unit. Linear movement of the translation member causes linear movement of the articulation links to cause articulation of a tool assembly of the disposable loading unit.

The surgical stapling apparatus also preferably includes a sensing mechanism for sensing the type of disposable loading unit secured to the elongated body of the apparatus. The sensing mechanism includes a sensing tube positioned within the elongated body to engage a disposable loading unit secured to the elongated body. A sensing cylinder connected to the sensing tube engages a locking ring having a tab portion configured to engage the articulation mechanism in a first position to prevent movement of the articulation lever. The locking ring is moved by the sensing cylinder when an articulating disposable loading unit is secured to the elongated body of the stapling apparatus to a second position to disengage the tab portion from the articulation mechanism to permit movement of the articulation lever. In contrast, a non-articulating disposable loading unit will not unlock the articulation lever.

BRIEF DESCRIPTION OF THE DRAWINGS

Various preferred embodiments are described herein with reference to the drawings:

FIG. 12a is a perspective view of a non-articulating disposable loading unit usable with the surgical stapling apparatus shown in FIG. 1;

FIG. 12b is a perspective view of the preferred articulating disposable loading unit of the surgical stapling apparatus shown in FIG. 1;

FIG. 27 is an enlarged perspective view with parts separated of the proximal housing portion and mounting assembly of the disposable loading unit shown in FIG. 19;

FIG. 28 is an enlarged perspective view of the mounting assembly of the disposable loading unit shown in FIG. 19 mounted to a distal end portion of the proximal housing portion;

FIG. 29 is an enlarged perspective view of the proximal housing portion and the mounting assembly of the disposable loading unit shown in FIG. 19 with the upper housing half removed;

FIG. 30 is a perspective view of the proximal housing portion and the mounting assembly of the disposable loading unit shown in FIG. 19 with the upper housing half removed;

FIG. 32 is an enlarged perspective view of the axial drive assembly shown in FIG. 31;

FIG. 33 is an enlarged perspective view of the proximal end of the axial drive assembly shown in FIG. 31 including the locking device;

FIG. 34 is an enlarged perspective view of the distal end of the axial drive assembly shown in FIG. 31;

FIG. 35 is an enlarged perspective view of the distal end of the elongated body of the stapling apparatus shown in FIG. 1;

FIG. 36 is an enlarged perspective view of the locking device shown in FIG. 33;

FIG. 37 is an enlarged perspective view of a lower housing half of the proximal housing portion of the disposable loading unit shown in FIG. 27;

FIG. 40 is a perspective view of the surgical stapling apparatus shown in with the disposable loading unit of FIG. 19 detached from the elongated body;

FIG. 41 is an enlarged perspective view of the disposable loading unit of FIG. 19 during attachment to the elongated body of the surgical stapling apparatus shown in FIG. 1;

FIG. 42 is another enlarged perspective view of the disposable loading unit of FIG. 19 during attachment to the elongated body of the surgical stapling apparatus shown in FIG. 1;

FIG. 43 is a cross-sectional view taken along section line 43—43 of FIG. 41;

FIG. 43a is a side cross-sectional view of the rotation knob, articulation mechanism, and sensing mechanism during insertion of a disposable loading unit into the elongated body of the surgical stapling apparatus;

FIG. 44 is a cross-sectional view taken along section line 44—44 of FIG. 42;

FIG. 51 is a side cross-sectional view of the distal end of the tool assembly of the stapling apparatus shown in FIG. 1 during firing of the apparatus;

FIG. 52 is a side cross-sectional view of the distal end of the tool assembly of the stapling apparatus shown in FIG. 1 after firing of the apparatus;

FIG. 54 is a side cross-sectional view of the handle assembly of the stapling apparatus during actuation of the emergency release button;

FIG. 58 is a perspective view of the surgical stapling apparatus during articulation of the tool assembly;

FIG. 59 is a perspective view of the surgical stapling apparatus during articulation and rotation of the tool assembly;

DETAILED DESCRIPTION OF PREFERRED EMBODIMENTS

Figure 1:
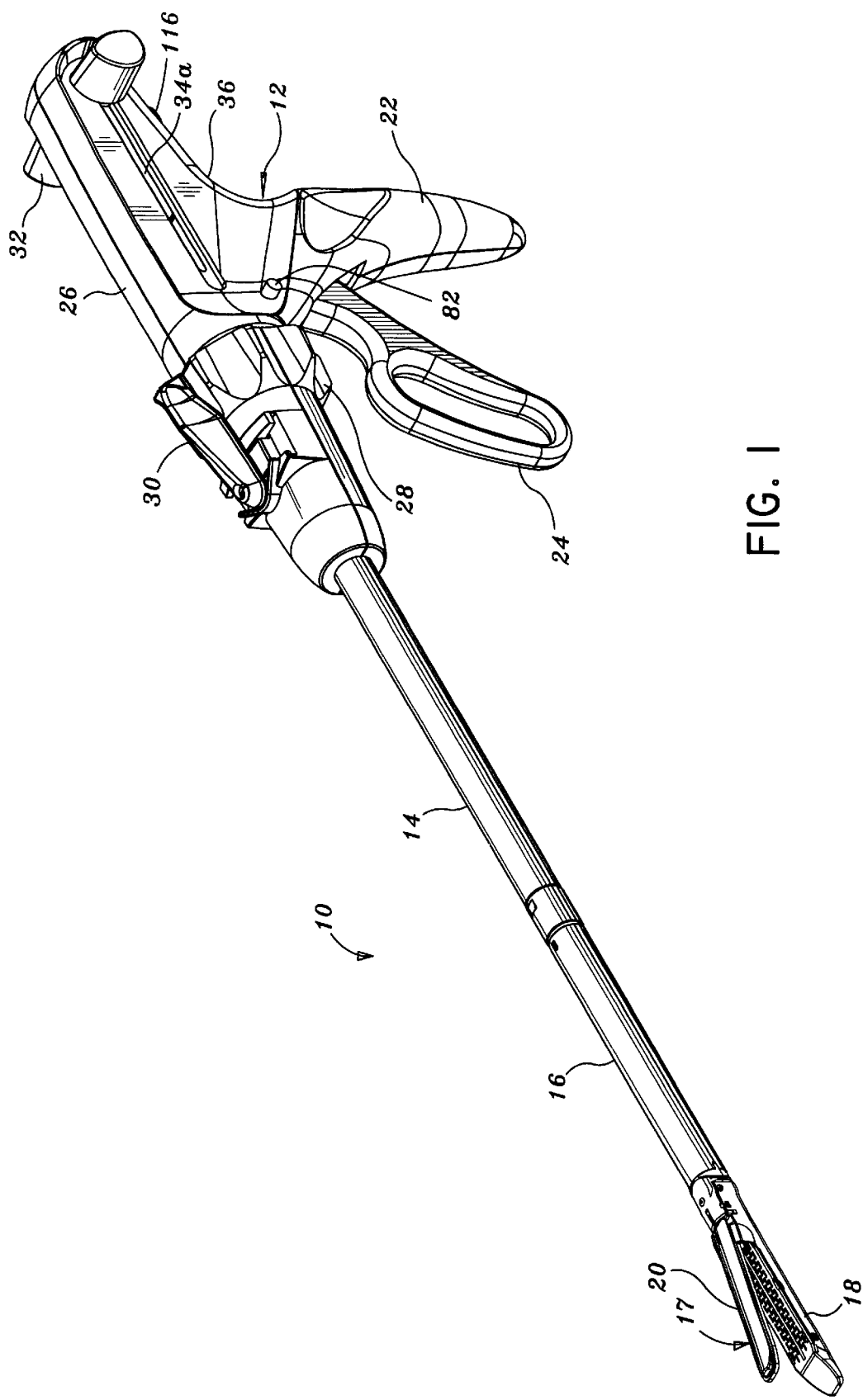
FIG. 1 is a perspective view of one preferred embodiment of the presently disclosed surgical stapling apparatus.

Preferred embodiments of the presently disclosed endoscopic surgical stapling apparatus will now be described in detail with reference to the drawings, in which like reference numerals designate identical or corresponding elements in each of the several views.

In the drawings and in the description that follows, the term "proximal", as is traditional, will refer to the end of the stapling apparatus which is closest to the operator, while the term distal will refer to the end of the apparatus which is furthest from the operator.

Figure 2:
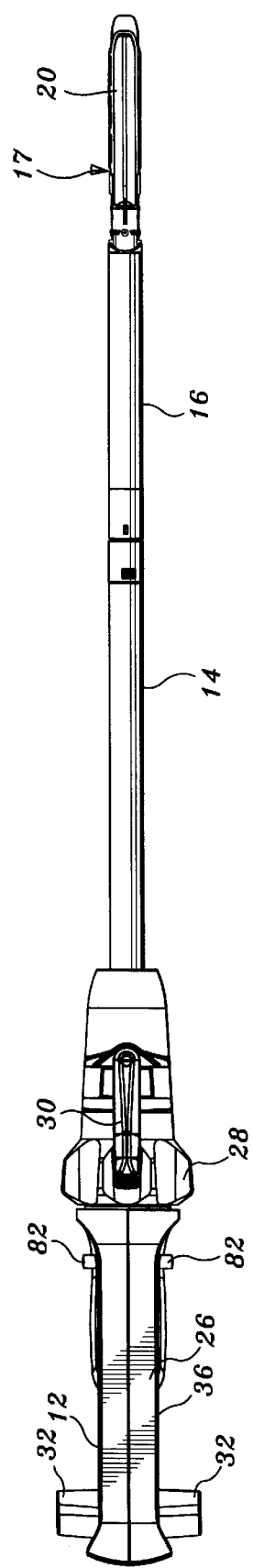
FIG. 2 is a top view of the surgical apparatus shown in FIG. 1.
Figure 3:
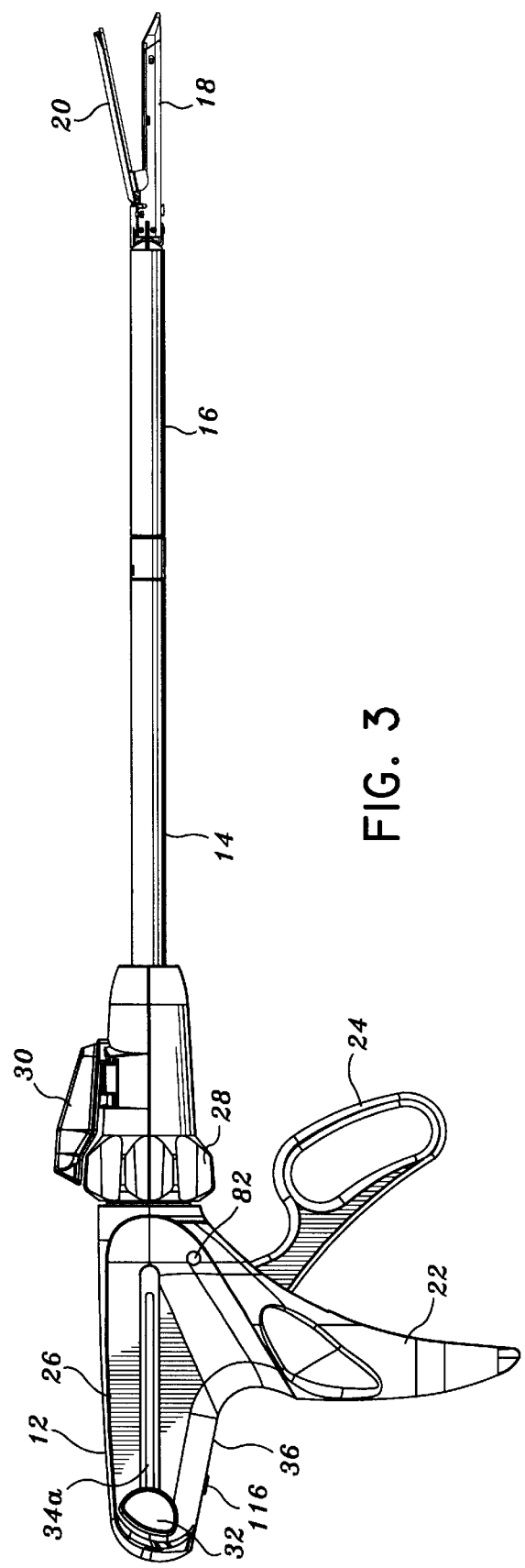
FIG. 3 is a side view of the surgical apparatus shown in FIG. 1.

FIGS. 1–3 illustrate one embodiment of the presently disclosed surgical stapling apparatus shown generally as 10. Briefly, surgical stapling apparatus 10 includes a handle assembly 12 and an elongated body 14. A disposable loading unit or DLU 16 is releasably secured to a distal end of elongated body 14. Disposable loading unit 16 includes a tool assembly 17 having a cartridge assembly 18 housing a plurality of surgical staples and an anvil assembly 20 movably secured in relation to cartridge assembly 18. Disposable loading unit 16 is configured to apply linear rows of staples measuring from about 30 mm to about 60 mm in length. Disposable loading units having linear rows of staples of other lengths are also envisioned, e.g., 45 mm. Handle assembly 12 includes a stationary handle member 22, a movable handle member 24, and a barrel portion 26. A rotatable member 28 is preferably mounted on the forward end of barrel portion 26 to facilitate rotation of elongated body 14 with respect to handle assembly 12. An articulation lever 30 is also preferably mounted on the forward end of barrel portion 26 adjacent rotatable knob 28 to facilitate articulation of tool assembly 17. A pair of retraction knobs 32 are movably positioned along barrel portion 26 to return surgical stapling apparatus 10 to a retracted position, as will be described in detail below.

Figure 4:
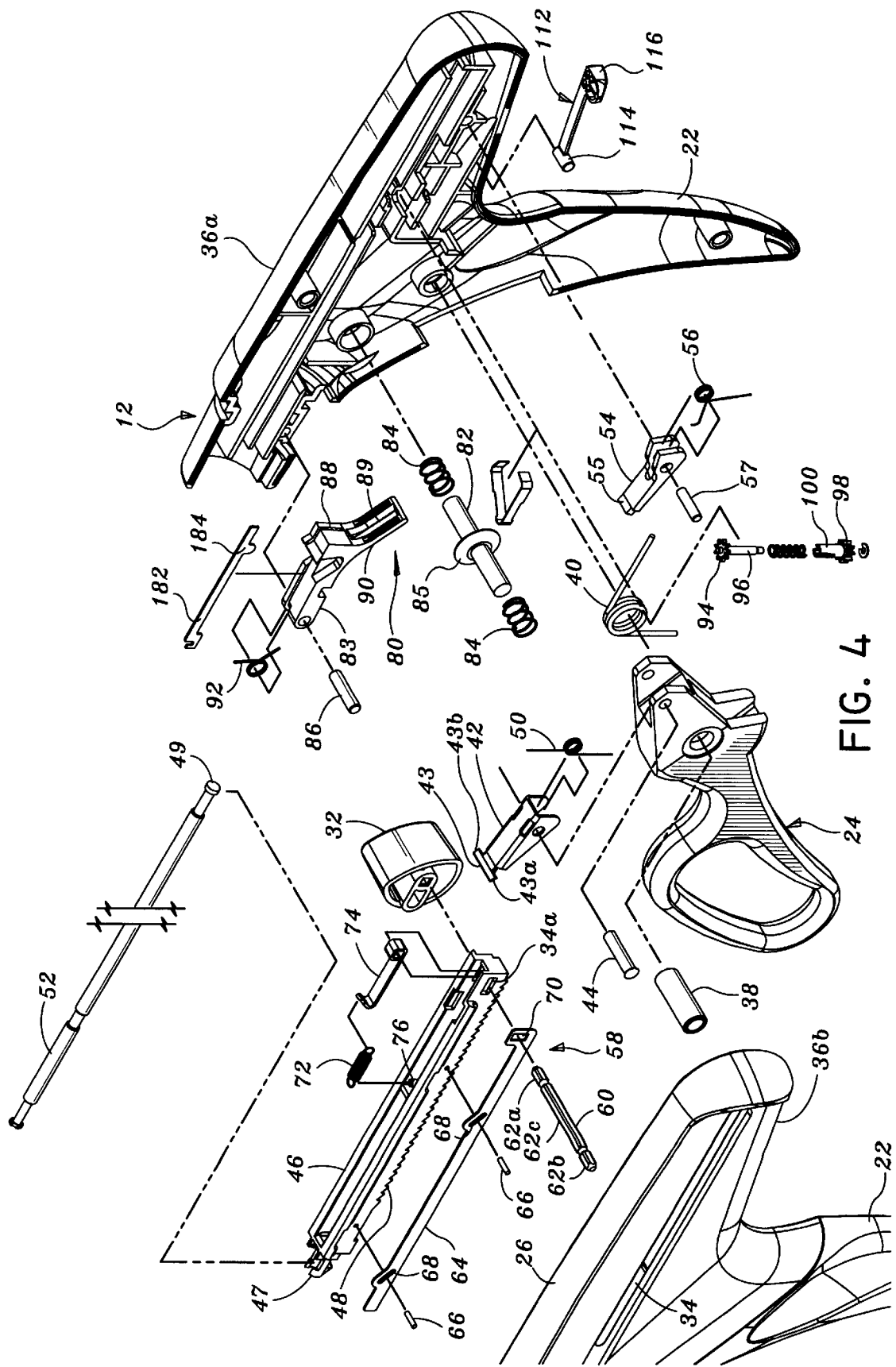
FIG. 4 is a perspective view with parts separated of the handle assembly of the surgical apparatus shown in FIG. 1.

Referring to FIG. 4, handle assembly 12 includes housing 36, which is preferably formed from molded housing half-sections 36a and 36b, which forms stationary handle member 22 and barrel portion 26 of handle assembly 12 (See FIG. 1). Movable handle member 24 is pivotably supported between housing half-sections 36a and 36b about pivot pin 38. A biasing member 40, which is preferably a torsion spring, biases movable handle 24 away from stationary handle 22. An actuation shaft 46 is supported within barrel portion 26 of housing 36 and includes a toothed rack 48. A driving pawl 42 having a rack engagement finger 43 with laterally extending wings 43a and 43b is pivotably mounted to one end of movable handle 24 about a pivot pin 44. A biasing member 50, which is also preferably a torsion spring, is positioned to urge engagement finger 43 of driving pawl 42 towards toothed rack 48 of actuation shaft 46. Movable handle 24 is pivotable to move engagement finger 43 of driving pawl 42 into contact with toothed rack 48 of actuation shaft 46 to advance the actuation shaft linearly in the distal direction. The forward end of actuation shaft 46 rotatably receives the proximal end 49 of a control rod 52 such that linear advancement of actuation shaft 46 causes corresponding linear advancement of control rod 52. A locking pawl 54 having a rack engagement member 55 is pivotably mounted within housing 36 about pivot pin 57 and is biased towards toothed rack 48 by biasing member 56, which is also preferably a torsion spring. Engagement member 55 of locking pawl 54 is movable into engagement with toothed rack 48 to retain actuation shaft 46 in a longitudinally fixed position.

A retraction mechanism 58 which includes a pair of retractor knobs 32 (See FIG. 1) is connected to the proximal end of actuation shaft 46 by a coupling rod 60. Coupling rod 60 includes right and left engagement portions 62a and 62b for receiving retractor knobs 32 and a central portion 62c which is dimensioned and configured to translate within a pair of longitudinal slots 34a formed in actuation shaft 46 adjacent the proximal end thereof. A release plate 64 is operatively associated with actuation shaft 46 and is mounted for movement with respect thereto in response to manipulation of retractor knobs 32. A pair of spaced apart pins 66 extend outwardly from a lateral face of actuation shaft 46 to engage a pair of corresponding angled cam slots 68 formed in release plate 64. Upon rearward movement of retractor knobs 32, pins 66 can release plate 64 downwardly with respect to actuation shaft 46 and with respect to toothed rack 48 such that the bottom portion of release plate 64 extends below toothed rack 48 to disengage engagement finger 43 of driving pawl 42 from toothed rack 48. A transverse slot 70 is formed at the proximal end of release plate 64 to accommodate the central portion 62c of coupling rod 60, and elongated slots 34 (See FIG. 1) are defined in the barrel section 26 of handle assembly 12 to accommodate the longitudinal translation of coupling rod 60 as retraction knobs 32 are pulled rearwardly to retract actuation shaft 46 and thus retract control rod 52 rearwardly. Actuation shaft 46 is biased proximally by spring 72 which is secured at one end to coupling rod portion 62 via connector 74 and at the other end to post 76 on actuation shaft 46.

Figure 5:
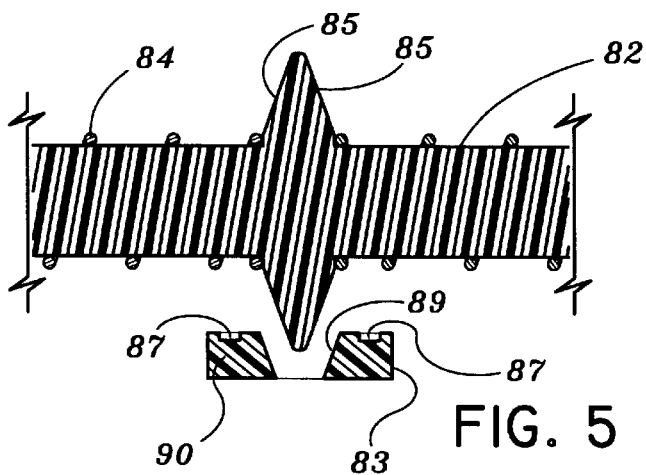
FIG. 5 is a cross-sectional view of a portion of the firing lockout mechanism shown in FIG. 4.

Referring also to FIG. 5, handle assembly 12 includes a firing lockout assembly 80 which includes a plunger 82 and a pivotable locking member 83. Plunger 82 is biased to a central position by biasing springs 84 and includes annular tapered camming surfaces 85. Each end of plunger 82 extends through housing 36 (See FIG. 1) adjacent an upper end of stationary handle 22. Pivotable locking member 83 is pivotably attached at its distal end between housing halfsections 36a and 36b about pivot pin 86 and includes a locking surface 88 and proximal extension 90 having a slot 89 formed therein. Locking member 83 is biased by spring 92 counter-clockwise (as viewed in FIG. 4) to move locking surface 88 to a position to abut the distal end of actuation shaft 46 to prevent advancement of shaft 46 and subsequent firing of stapling apparatus 10. Annular tapered camming surface 85 is positioned to extend into tapered slot 89 in proximal extension 90. Lateral movement of plunger 82 in either direction against the bias of either spring 84 moves tapered camming surface 85 into engagement with the sidewalls of tapered slot 89 to pivot locking member 83 clockwise about pivot pin 86, as viewed in FIG. 4, to move blocking surface 88 to a position to permit advancement of actuation shaft 46 and thus firing of stapling apparatus 10. Blocking surface 88 is retained in this position by recesses 87 which receive the tapered tip of camming surface 85 to lock locking member 83 in a counter-clockwise position. Operation of firing lockout assembly 80 will be further illustrated below.

Figure 6:
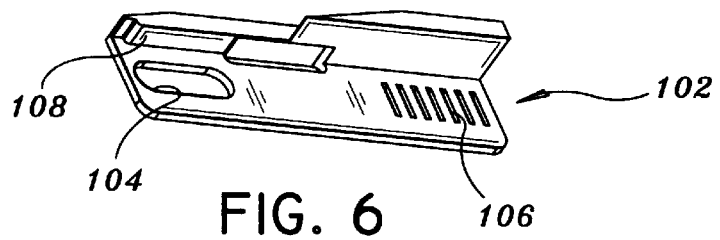
FIG. 6 is a perspective of the slide plate of the anti-reverse clutch mechanism of the surgical apparatus.
Figure 7:
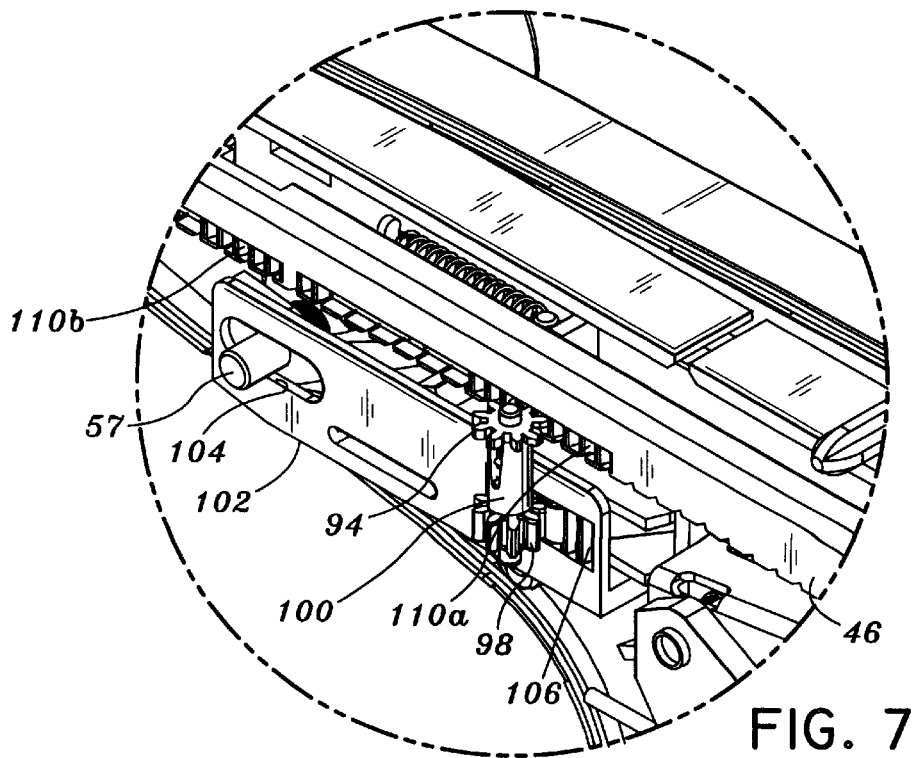
FIG. 7 is an enlarged perspective view of the anti- reverse clutch mechanism shown in FIG. 1.

Referring to FIGS. 4, 6, and 7, handle mechanism 12 also includes an anti-reverse clutch mechanism which includes a first gear 94 rotatably mounted on a first shaft 96, and second gear 98 mounted on a second shaft 100, and a slide plate 102 (FIGS. 6 and 7) slidably mounted within housing 36. Slide plate 102 includes an elongated slot 104 dimensioned and configured to be slidably positioned about locking pawl pivot pin 57, a gear plate 106 configured to mesh with the teeth of second gear 98, and a cam surface 108. In the retracted position, cam surface 108 of slide plate 102 engages locking pawl 54 to prevent locking pawl 54 from engaging toothed rack 48. Actuation shaft 46 includes a distal set of gear teeth 110a spaced from a proximal set of gear teeth 110b positioned to engage first gear 94 of actuation shaft 46 during movement of actuation shaft 46. When actuation shaft 46 is advanced by pivoting movable handle 24 about pivot pin 38, distal gear teeth 110a on actuation shaft 46 mesh with and rotate first gear 94 and first shaft 96. First shaft 96 is connected to second shaft 100 by spring clutch assembly such that rotation of first shaft 96 will cause corresponding rotation of second shaft 100. Rotation of second shaft 100 causes corresponding rotation of second gear 98 which is engaged with gear plate 106 on slide plate 102 to cause linear advancement of slide plate 102. Linear advancement of slide plate 102 is limited to the length of elongated slot 104. When slide plate has been advanced the length of slot 104, cam surface 108 releases locking pawl 54 such that it is moved into engagement with toothed rack 48. Continued advancement of actuation shaft 46 eventually moves gear teeth 110b into engagement with gear plate 106. However, since slide plate 102 is longitudinally fixed in position, the spring clutch is forced to release, such that continued distal advancement of actuation shaft 46 is permitted.

When actuation shaft 46 is returned to the retracted position (by pulling retraction knobs 34 proximally, as discussed above) gear teeth 110b engage first gear 94 to rotate second gear 98 in the reverse direction to retract slide member 102 proximally within housing 36. Proximal movement of slide member 102 advances cam surface 108 into locking pawl 54 prior to engagement between locking pawl 54 and toothed rack 48 to urge locking pawl 54 to a position to permit retraction of actuation shaft 46.

Referring again to FIG. 4, handle assembly 12 includes an emergency return button 112 pivotally mounted within housing 36 about a pivot member 114 supported between housing half-sections 36a and 36b. Return button 112 includes an externally positioned member 116 positioned on the proximal end of barrel portion 26. Member 116 is movable about pivot member 114 into engagement with the proximal end of locking pawl 54 to urge rack engagement member 55 out of engagement with toothed rack 48 to permit retraction of actuation shaft 46 during the firing stroke of the stapling apparatus 10. As discussed above, during the clamping portion of advancement of actuation shaft 46, slide plate 102 disengages pawl 54 from rack 48 and thus actuation of return button 112 is not necessary to retract the actuation shaft 46.

Figure 8:
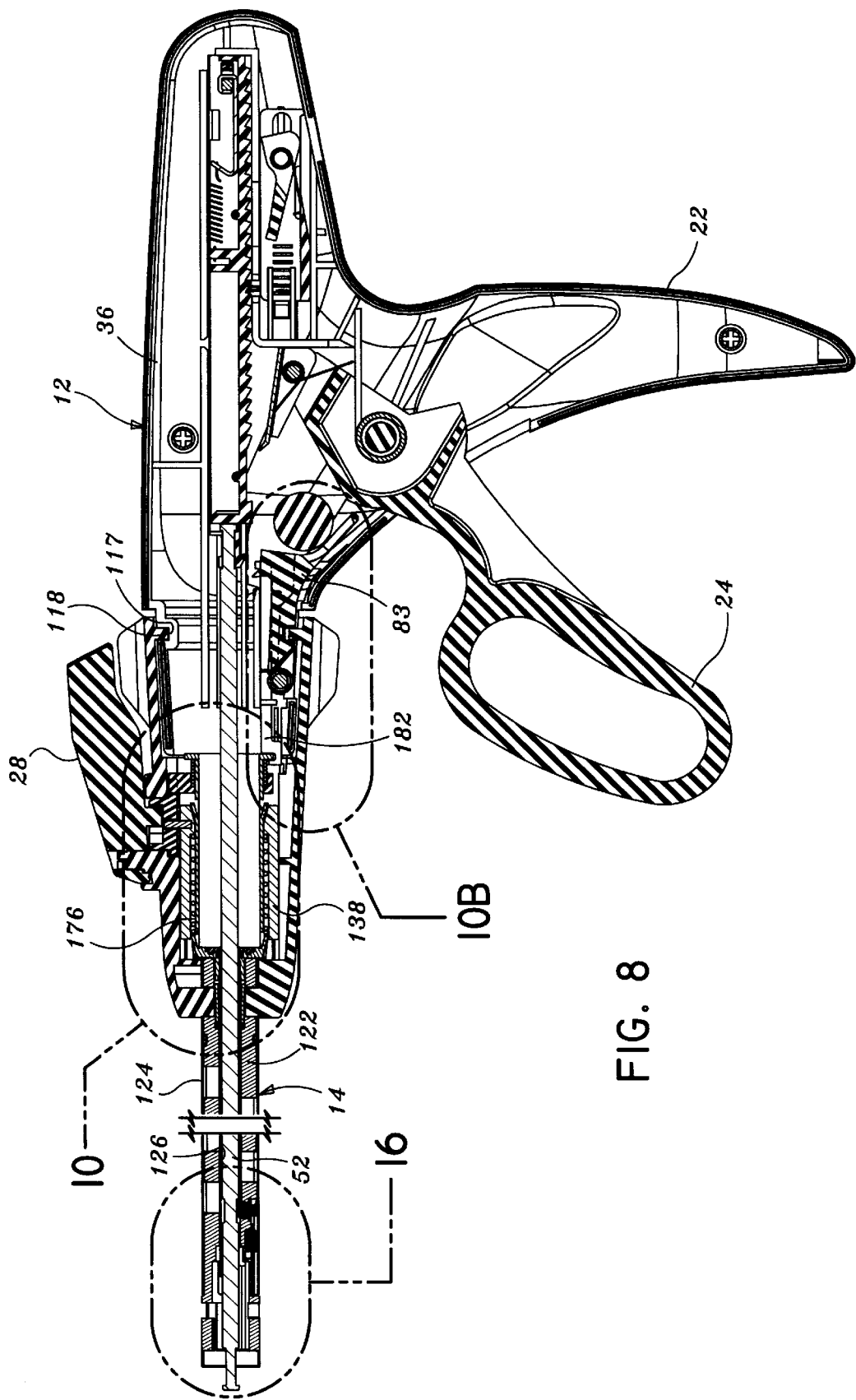
FIG. 8 is a side cross-sectional view of the surgical stapling apparatus shown in FIG. 1 in the non-actuated position with the disposable loading unit removed.
Figure 9:
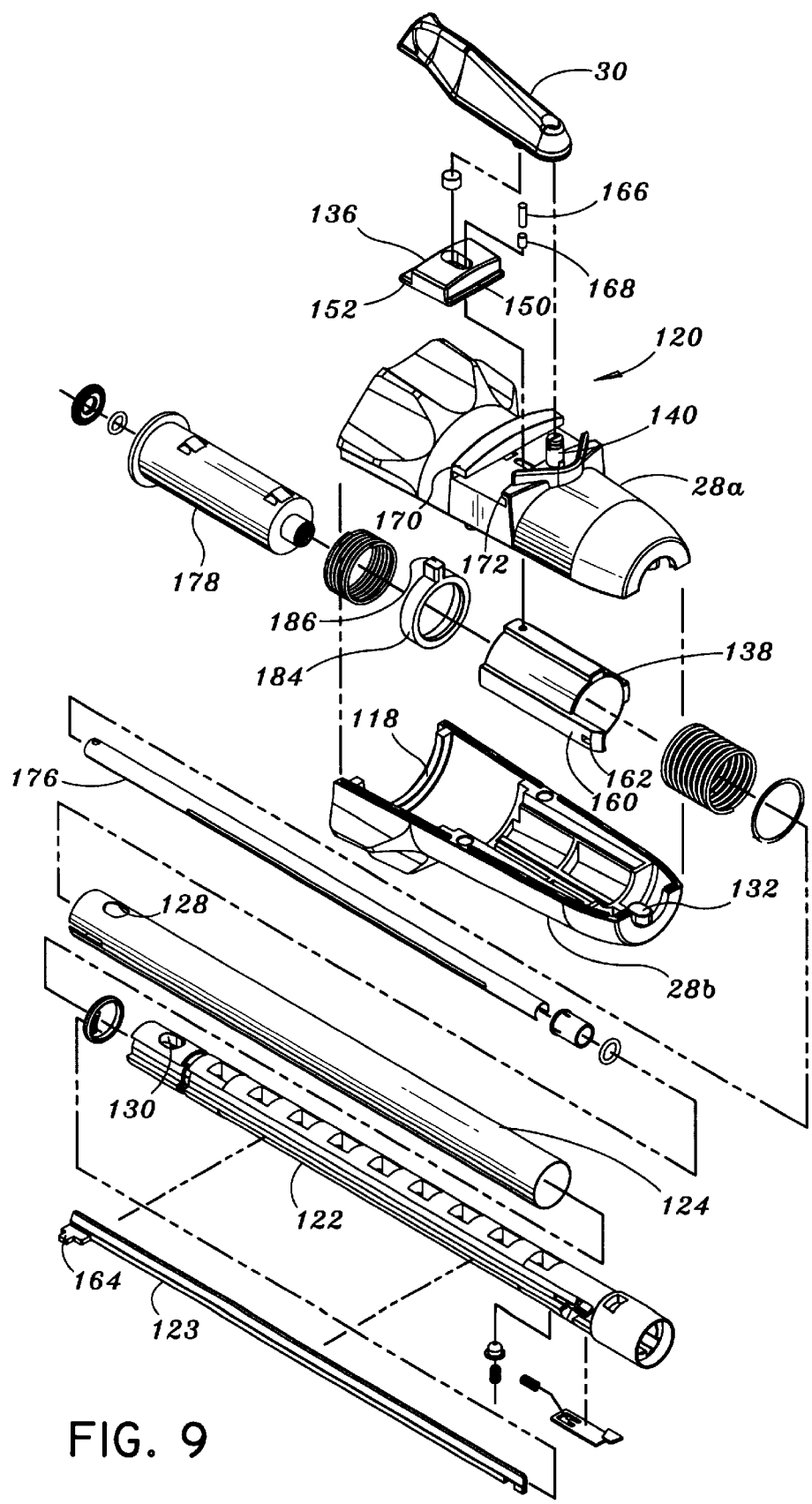
FIG. 9 is a perspective view with parts separated of the rotation member, the articulation mechanism, and the elongated body of the surgical stapling apparatus shown in FIG. 1.
Figure 10:
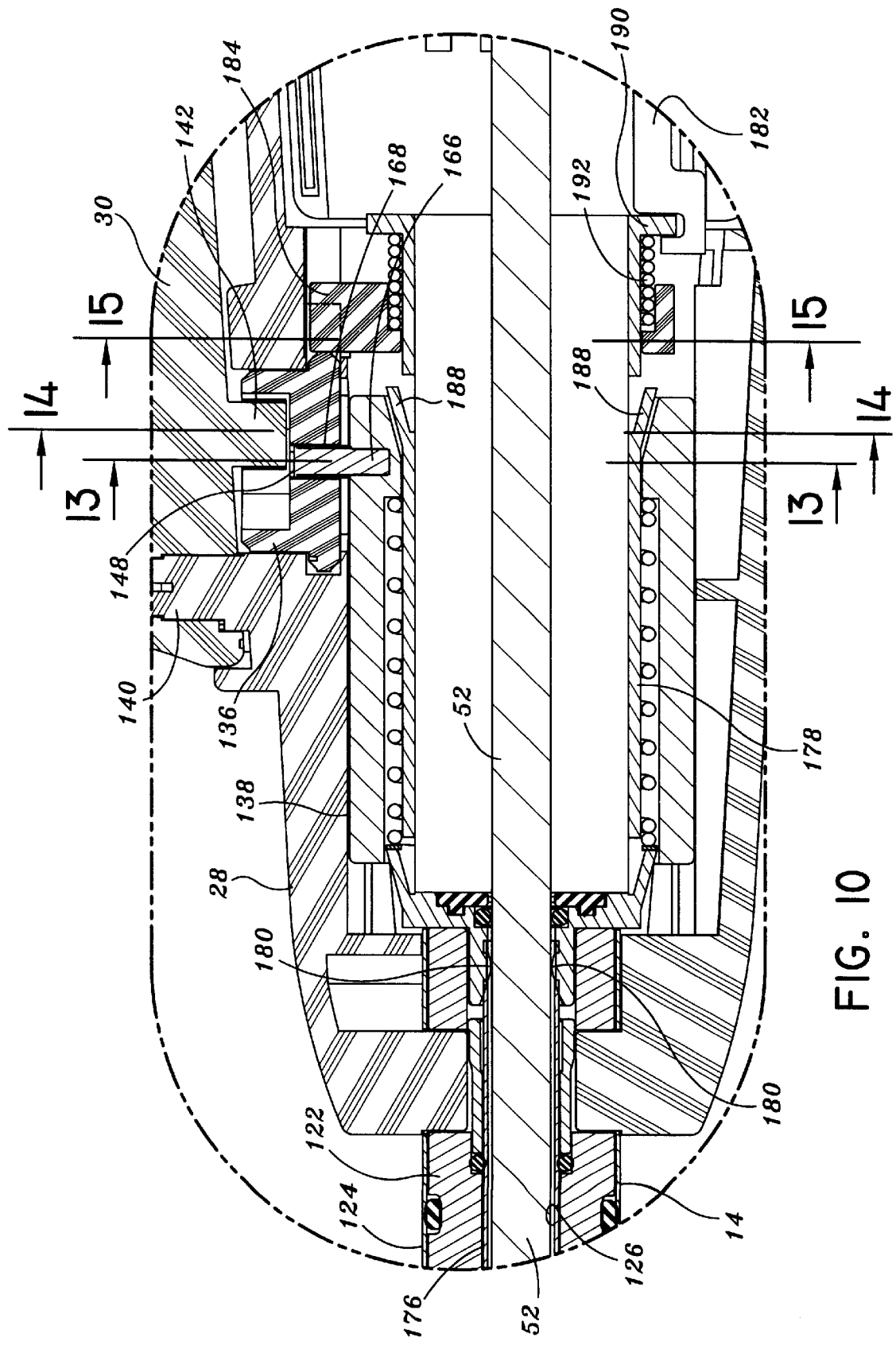
FIG. 10 is an enlarged view of the indicated area of detail shown in FIG. 8.

FIG. 8 illustrates the interconnection of elongated body 14 and handle assembly 12. Referring to FIGS. 8–10, housing 36 includes an annular channel 117 configured to receive an annular rib 118 formed on the proximal end of rotation member 28, which is preferably formed from molded half-sections 28a and 28b. Annular channel 117 and rib 118 permit relative rotation between rotation member 28 and housing 36. Elongated body 14 includes inner housing 122 and an outer casing 124. Inner housing 122 is dimensioned to be received within outer casing 124 and includes an internal bore 126 (FIG. 8) which extends therethrough and is dimensioned to slidably receive a first articulation link 123 and control rod 52. The proximal end of housing 122 and casing 124 each include a pair of diametrically opposed openings 130 and 128, respectively, which are dimensioned to receive radial projections 132 formed on the distal end of rotation member 28. Projections 132 and openings 128 and 130 fixedly secure rotation member 28 and elongated body 14 in relation to each others both longitudinally and rotatably. Rotation of rotation knob 28 with respect to handle assembly 12 thus results in corresponding rotation of elongated body 14 with respect to handle assembly 12.

An articulation mechanism 120 is supported on rotatable member 28 and includes articulation lever 30, a cam member 136, a translation member 138, and first articulation link 123 (FIG. 9). Articulation lever 30 is pivotably mounted about pivot member 140 which extends outwardly from rotation member 28 and is preferably formed integrally therewith. A projection 142 extends downwardly from articulation lever 30 for engagement with cam member 136.

Figure 12:
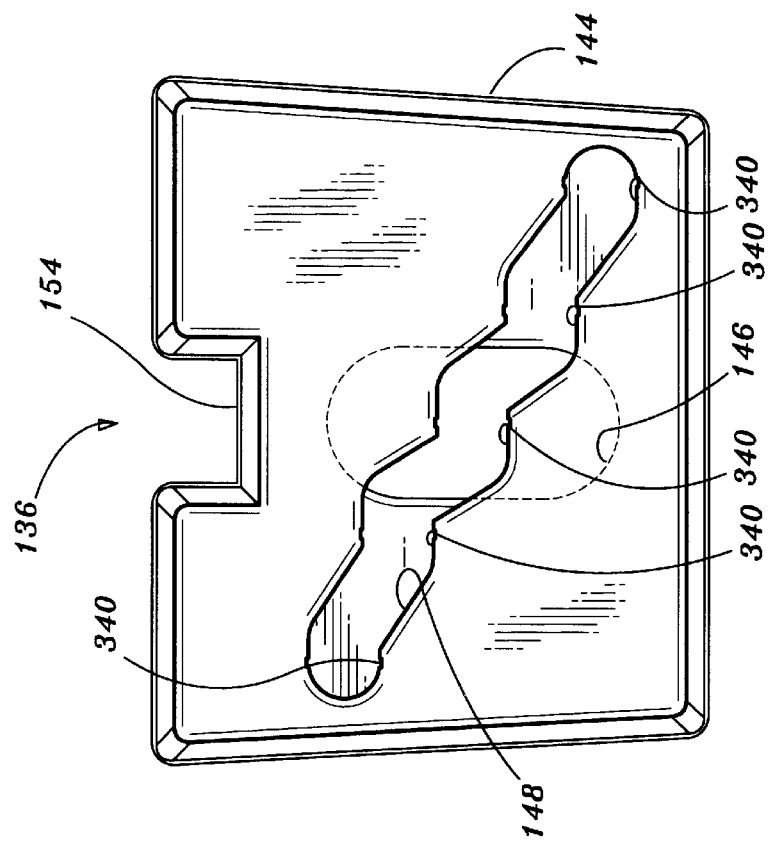
FIG. 12 is a top view of the cam member of the articulation mechanism of the surgical stapling apparatus shown in FIG. 1.
Figure 11:
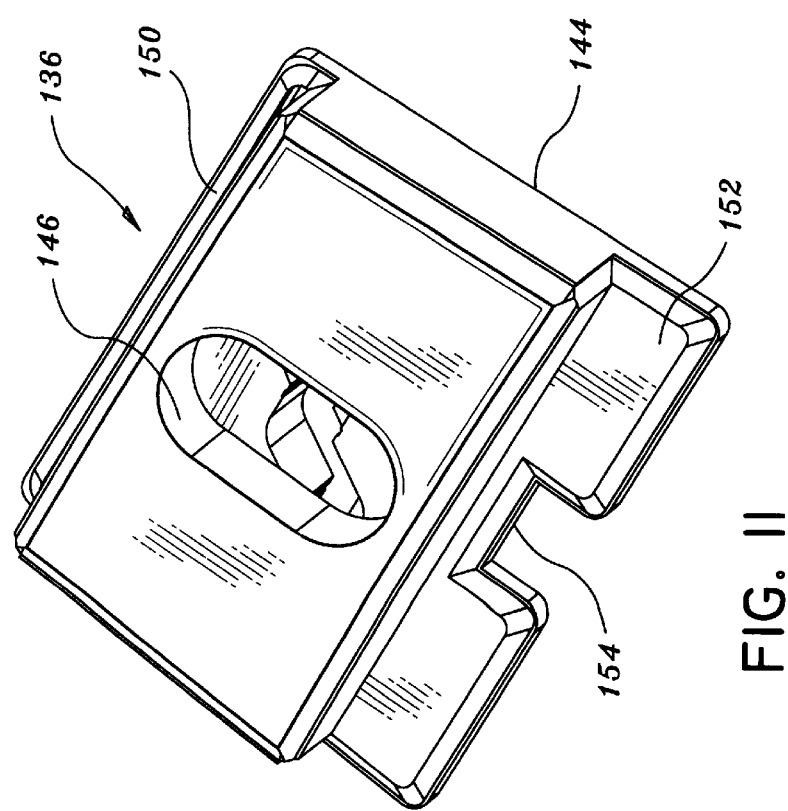
FIG. 11 is a perspective view of the cam member of the articulation mechanism of the surgical stapling apparatus shown in FIG. 1.

Referring temporarily to FIGS. 11 and 12, cam member 136 includes a housing 144 having an elongated slot 146 extending through one side thereof and a stepped camming surface 148 formed in the other side thereof. Each step of camming surface 148 corresponds to a particular degree of articulation of stapling apparatus 10. Although five steps are illustrated, fewer or more steps may be provided. Elongated slot 146 is configured to receive projection 142 formed on articulation lever 30. Housing 144 includes a distal stepped portion 150 and a proximal stepped portion 152. Proximal stepped portion 152 includes a recess 154.

Figure 10A:
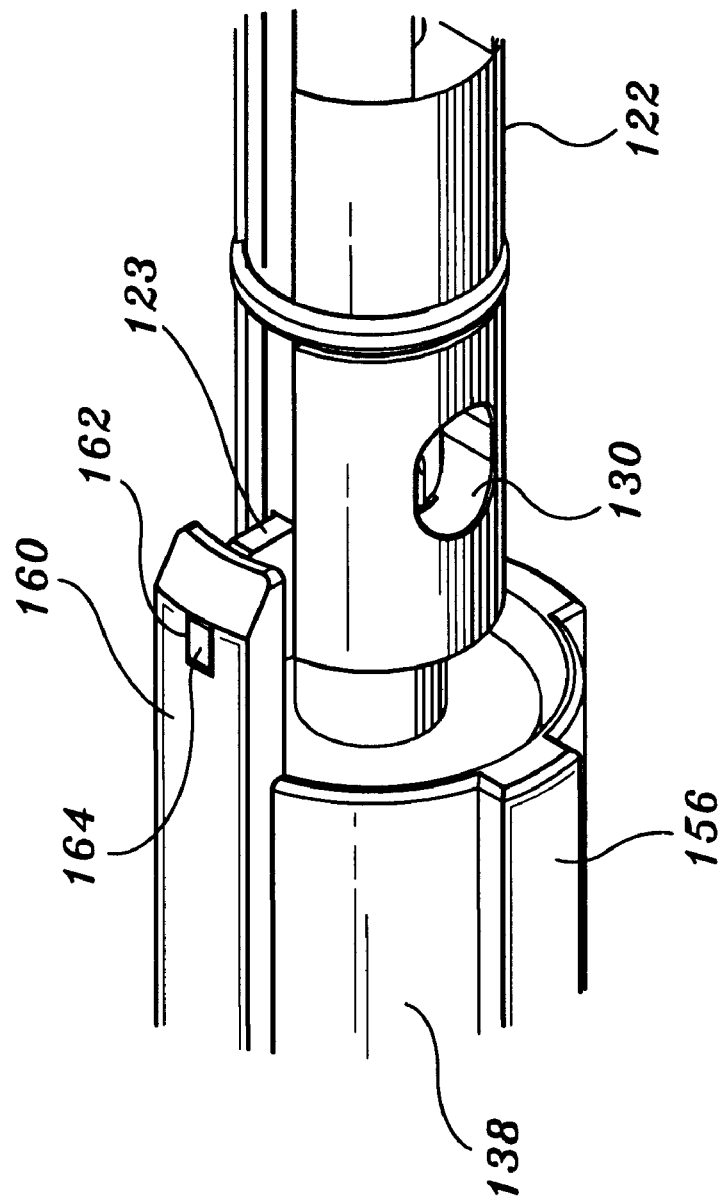
FIG. 10a is a perspective view of the translation member of the articulating mechanism and the proximal end of the elongated body of the surgical stapling apparatus shown in FIG. 1.
Figure 10B:
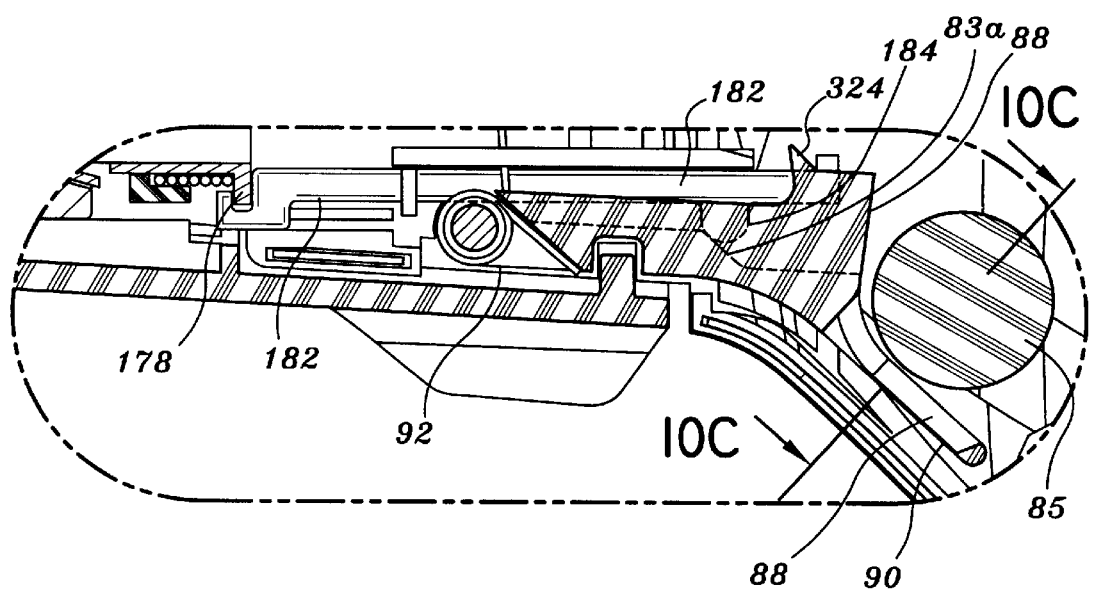
FIG. 10b is an enlarged cross-sectional view of the indicated area of detail of FIG. 8.
Figure 10C:
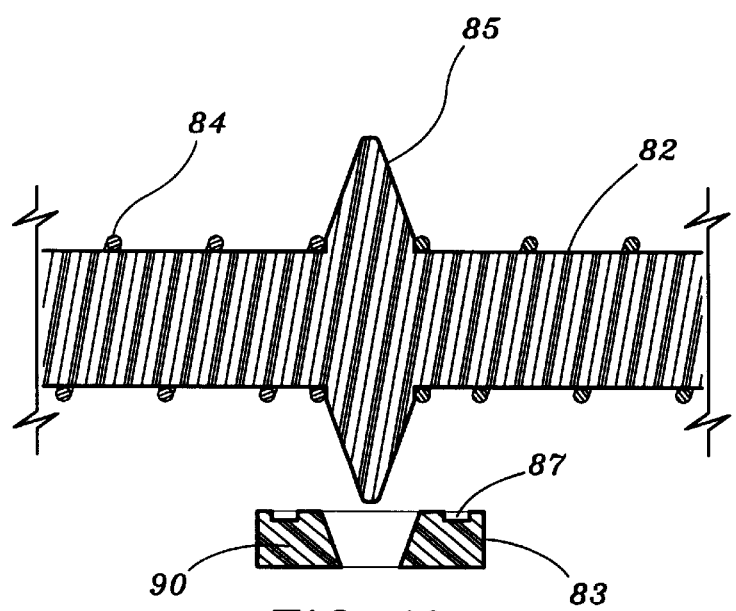
FIG. 10c is a cross-sectional view along section line 10c—10c of FIG. 8.
Figure 13:
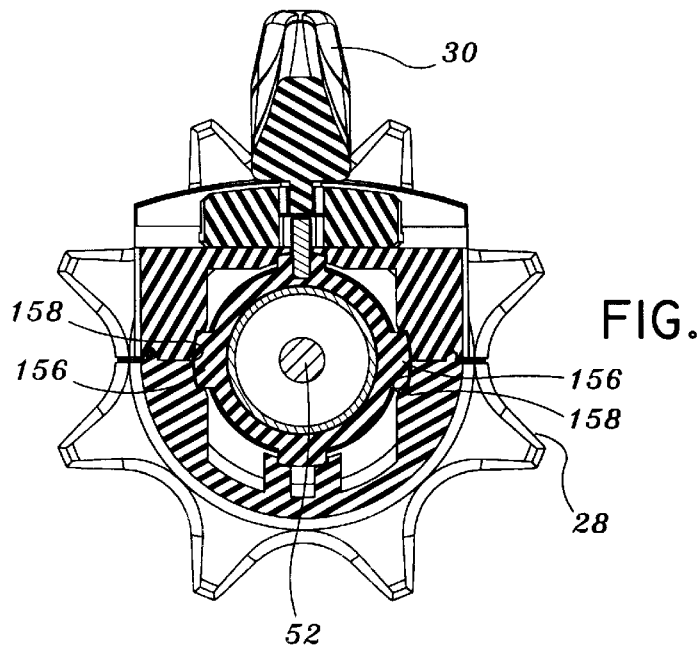
FIG. 13 is a cross-sectional view taken along section line 13—13 of FIG. 10.
Figure 14:
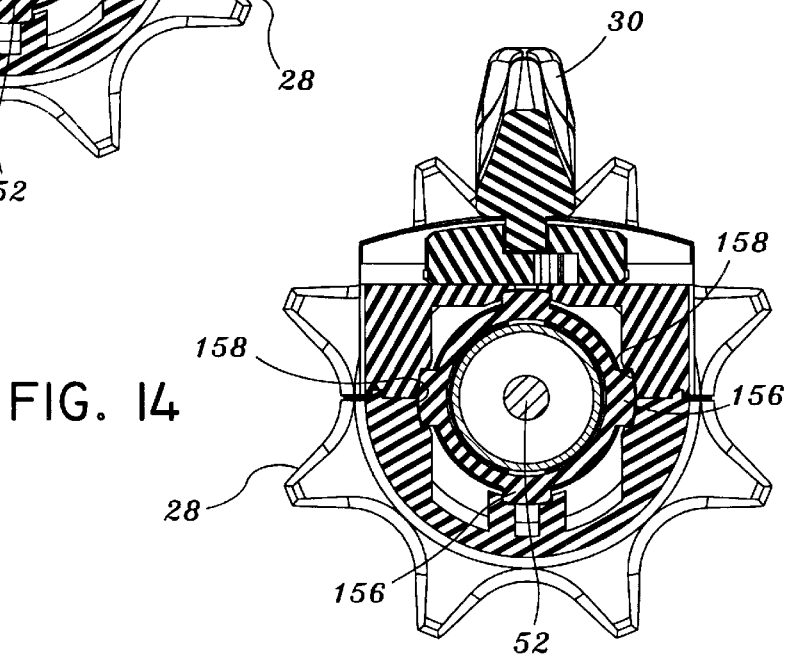
FIG. 14 is a cross-sectional view taken along section line 14—14 of FIG. 10.
Figure 15:
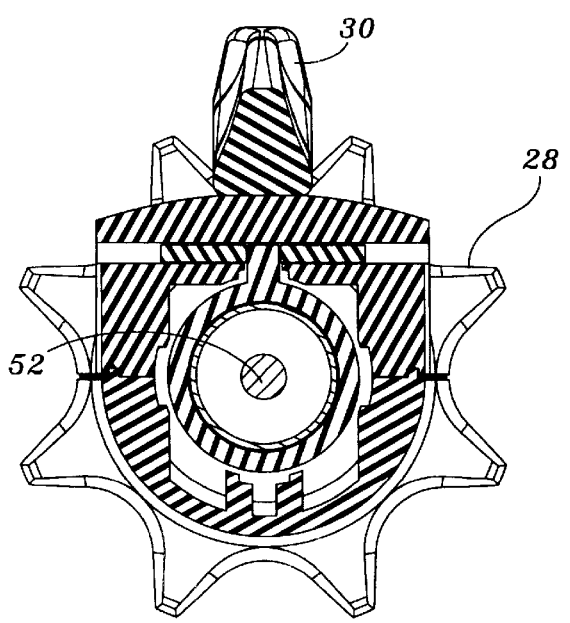
FIG. 15 is a cross-sectional view taken along section line 15—15 of FIG. 10.

Referring again to FIGS. 8–10 and also to FIGS. 13–15, translation member 138 includes a plurality of ridges 156 which are configured to be slidably received within grooves 158 formed along the inner walls of rotation member 28. Engagement between ridges 156 and grooves 158 prevent relative rotation of rotation member 28 and translation member 138 while permitting relative linear movement. The distal end of translation member 138 includes arm 160 which includes an opening 162 configured to receive a finger 164 extending from the proximal end of articulation link 123 (See FIG. 10a). A pin 166 having a housing 168 constructed from a non-abrasive material, e.g., teflon, is secured to translation member 138 and dimensioned to be received within stepped camming surface 148.

In an assembled condition, proximal and distal stepped portions 150 and 152 of cam member 136 are positioned beneath flanges 170 and 172 formed on rotation member 28 to restrict cam member 136 to transverse movement with respect to the longitudinal axis of stapling apparatus 10. When articulation lever 30 is pivoted about pivot member 140, cam member 136 is moved transversely on rotation member 28 to move stepped camming surface 148 transversely relative to pin 166, forcing pin 166 to move proximally or distally along stepped cam surface 148. Since pin 166 is fixedly attached to translation member 138, translation member 138 is moved proximally or distally to effect corresponding proximal or distal movement of first actuation link 123.

Referring to FIGS. 8–10 and 16, a disposable loading unit sensing mechanism extends within stapling apparatus 10 from elongated body 14 into handle assembly 12. The sensing mechanism includes a sensor tube 176 which is slidably supported within bore 26 of elongated body 14. The distal end of sensor tube 176 is positioned towards the distal end of elongated body 14 and the proximal end of sensor tube 176 is secured within the distal end of a sensor cylinder 176 via a pair of nubs 180. The distal end of a sensor link 182 is secured to the proximal end of sensor cylinder 178. Sensor link 182 (See FIGS. 8a and 8c) has a bulbous end 184 which engages a camming surface 83a on pivotable locking member 83. When a disposable loading unit (not shown) is inserted in the distal end of elongated body 14, the disposable loading unit engages the distal end 177 of sensor tube 176 to drive sensor tube 176 proximally, and thereby drive sensor cylinder 178 and sensor link 182 proximally. Movement of sensor link 182 proximally causes bulbous end 184 of:sensor 182 to move distally of camming surface 83a to allow locking member 83 to pivot under the bias of spring 92 from a position permitting firing of stapling apparatus 10 to a blocking position, wherein blocking member 83 is positioned to engage actuation shaft 46 and prevent firing of stapling apparatus 10. Sensor link 182 and locking member 83 function to prevent firing of surgical stapling apparatus 10 after a disposable loading unit has been secured to elongated body 14, without first operating firing lockout assembly 80. It is noted that movement of link 182 proximally permits locking member 83 to move to its position shown in FIG. 5.

Referring again to FIGS. 9–12, cam member 136 includes recess 154. A locking ring 184 having a nub portion 186 configured to be received within recess 154 is positioned about sensor cylinder 178 between a control tab portion 188 and a proximal flange portion 190. A spring 192 positioned between flange portion 190 and locking ring 184 urges locking ring distally about sensor cylinder 178. When an articulating disposable loading unit 16b having an extended insertion tip 193 is inserted into the distal end of elongated body 14 of stapling apparatus 10, insertion tip 193 causes tab portion 188 to move proximally into engagement with locking ring 184 to urge locking ring 184 and nub 186 proximally of recess 154 in cam member 136 (See FIG. 12b). With nub 186 positioned proximally of recess 154, cam member 136 is free to move transversely to effect articulation of stapling apparatus 10. A non-articulating disposable loading unit does not have an extended insertion tip (See FIG. 12a). As such, when a non-articulating disposable loading unit is inserted in elongated body 14, sensor cylinder 178 is not retracted proximally a sufficient distance to move nub 186 from recess 154. Thus, cam member 136 is prevented from moving transversely by nub 186 of locking ring 184 which is positioned in recess 154 and articulation lever 30 is locked in its central position.

Figure 16:
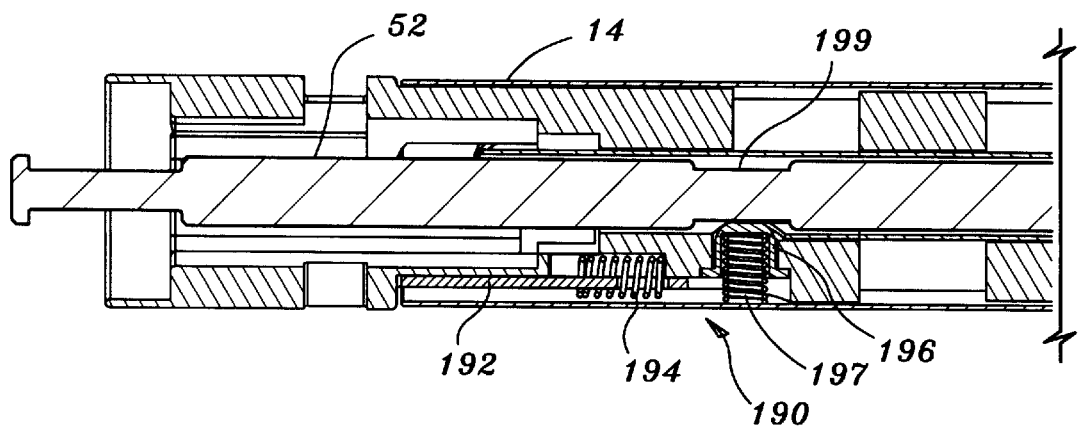
FIG. 16 is an enlarged view of the indicated area of detail shown in FIG. 8.
Figure 17:
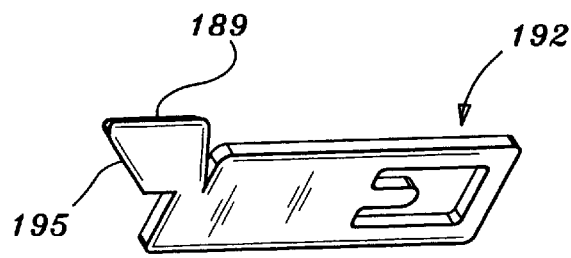
FIG. 17 is a side perspective view of the blocking plate of the surgical stapling apparatus shown in FIG. 1.
Figure 18:
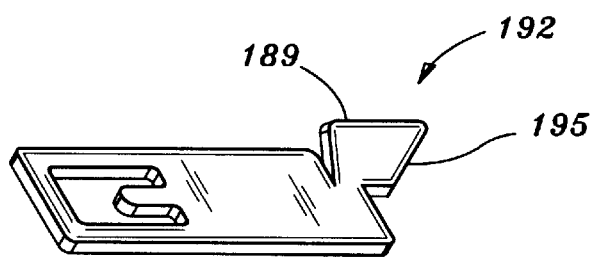
FIG. 18 is a top perspective view of the blocking plate of the surgical stapling apparatus shown in FIG. 1.

Referring to FIGS. 16–18, the distal end of elongated body 14 includes a control rod locking mechanism 190 which is activated during insertion of a disposable loading unit into elongated body 14. Control rod locking mechanism 190 includes a blocking plate 192 which is biased distally by a spring 194 and includes a proximal finger 189 having angled cam surface 195. A semi-circular engagement member 196 is biased transversely towards control rod 52 by a spring 197. Control rod 52 includes an annular recess 199 configured to receive engagement member 196. Blocking plate 192 is movable from a distal position spaced from engagement member 196 to a proximal position located behind engagement member 196. In the proximal position, engagement member 196 is prevented from being biased from recess 199 by engagement with blocking plate 192. During insertion of a disposable loading unit 16 (See FIG. 1) into the distal end of elongated body 14, as will be described in further detail below, cam surface 195 of blocking plate 192 is engaged by a nub 254 (FIG. 30) on the disposable loading unit 16 as the disposable loading unit is rotated into engagement with elongated body 14 to urge plate 192 to the proximal position. Engagement member 196, which is positioned within recess 199, is retained therein by blocking plate 192 while nub 254 engages cam surface 195 to prevent longitudinal movement of control rod 52 during assembly. When the disposable loading unit 16 is properly positioned with respect to the elongated body 14, nub 254 on the proximal end of the disposable loading unit 16 passes off cam surface 195 allowing spring 194 to return blocking plate 192 to its distal position to permit subsequent longitudinal movement of control rod 52. It is noted that when the disposable loading unit nub passes off cam surface 195, an audible clicking sound is produced indicating that the disposable loading unit 16 is properly fastened to the elongated body 14.

Figure 19:
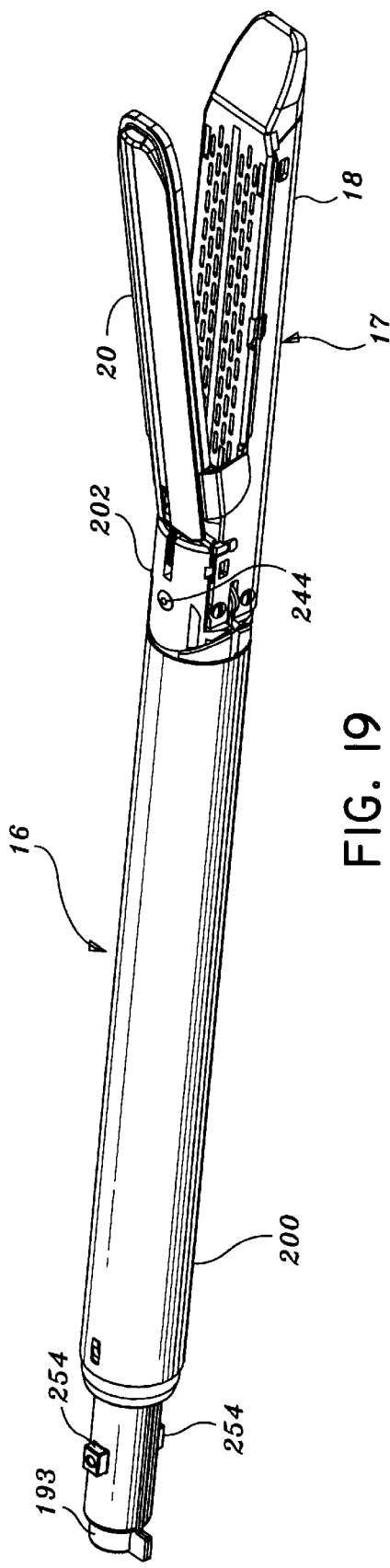
FIG. 19 is a perspective view of a disposable loading unit usable with the surgical stapling apparatus of FIG. 1.
Figure 20:
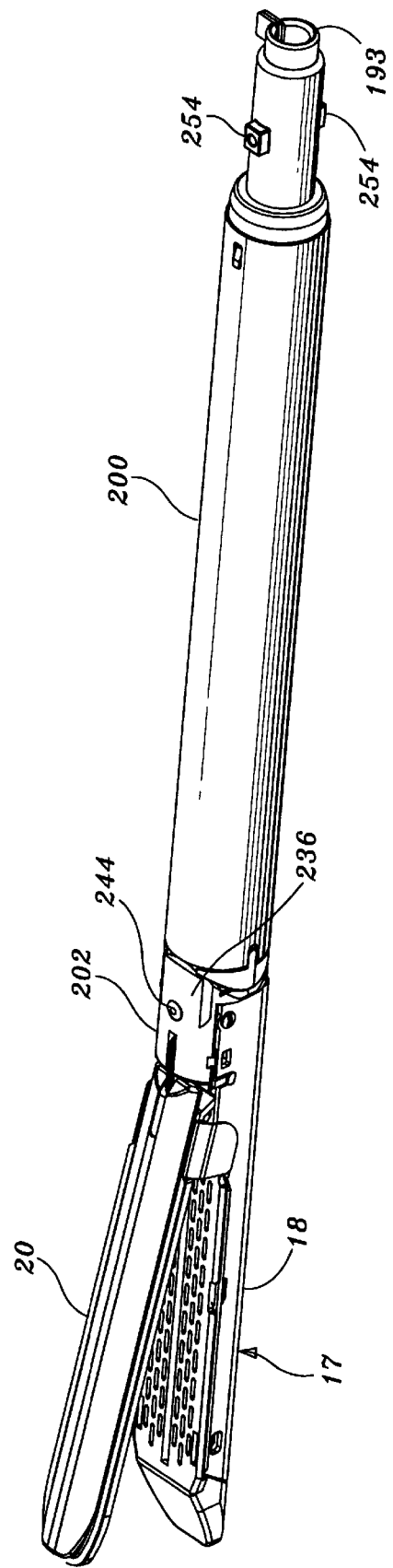
FIG. 20 is another perspective view of a disposable loading unit usable with the surgical stapling apparatus of FIG. 1.
Figure 21:
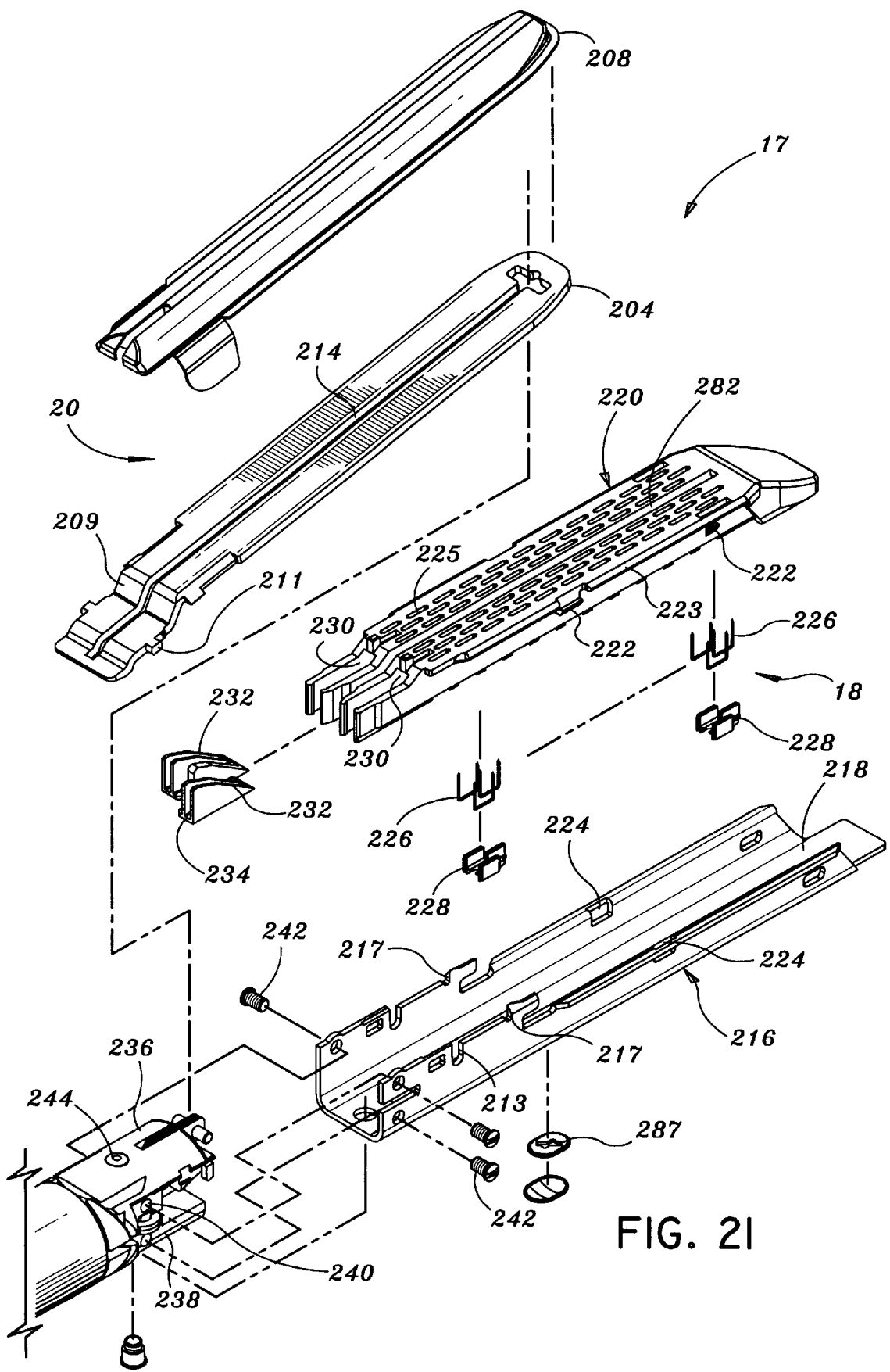
FIG. 21 is a perspective view of the tool assembly of the surgical stapling apparatus of FIG. 1 with parts separated.
Figure 22:
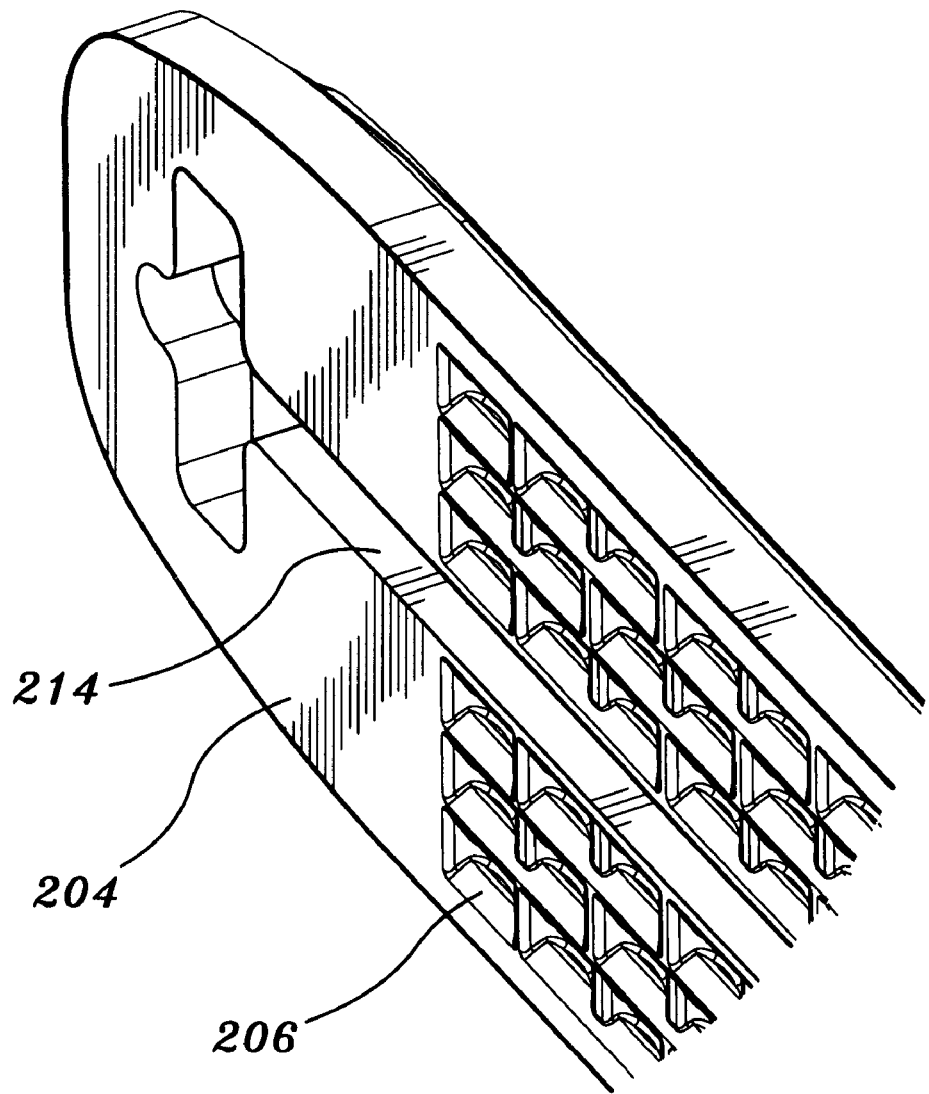
FIG. 22 is an enlarged perspective view of the distal end of the anvil assembly showing a plurality of staple deforming cavities.
Figure 23:
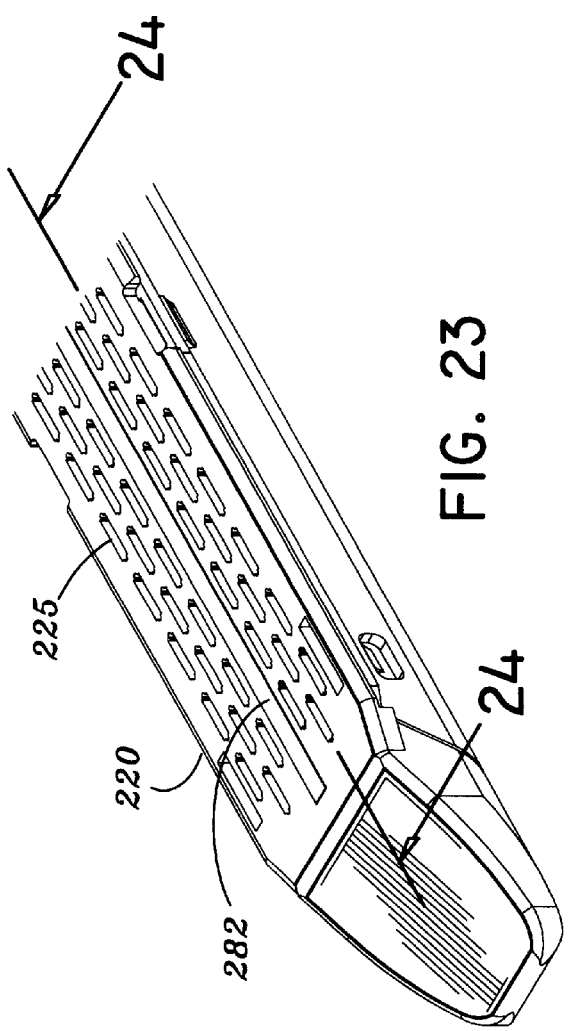
FIG. 23 is an enlarged perspective view of the distal end of the staple cartridge of the surgical stapling apparatus shown in FIG. 1.
Figure 24:
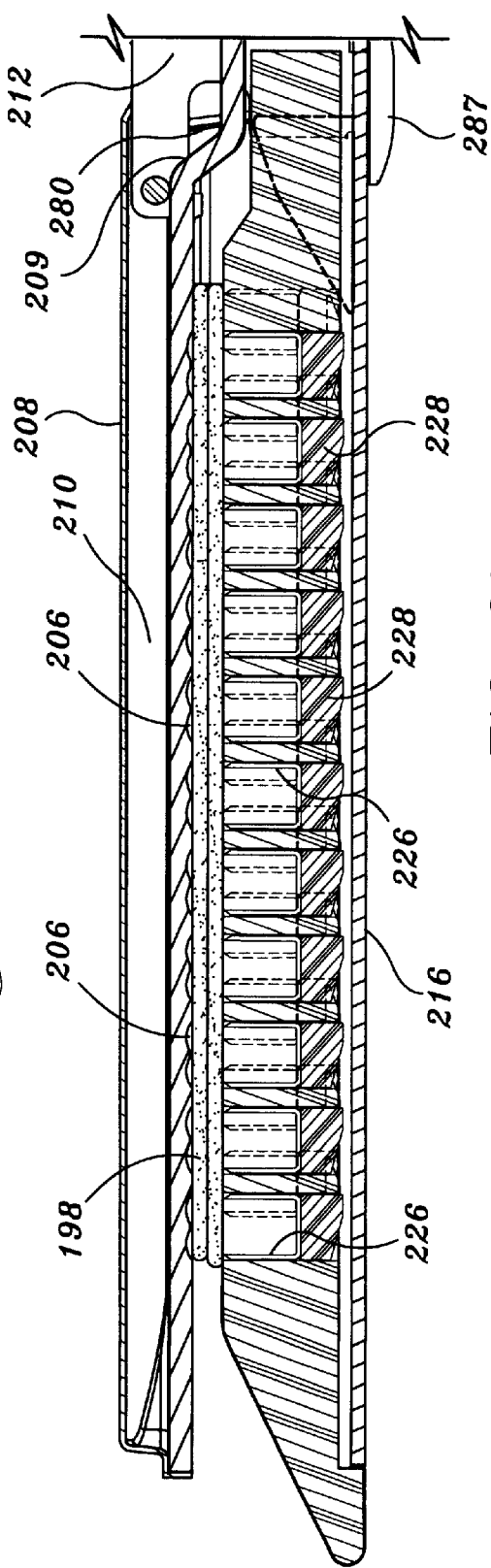
FIG. 24 is a side cross-sectional view taken along section line 24—24 of FIG. 23.
Figure 25:
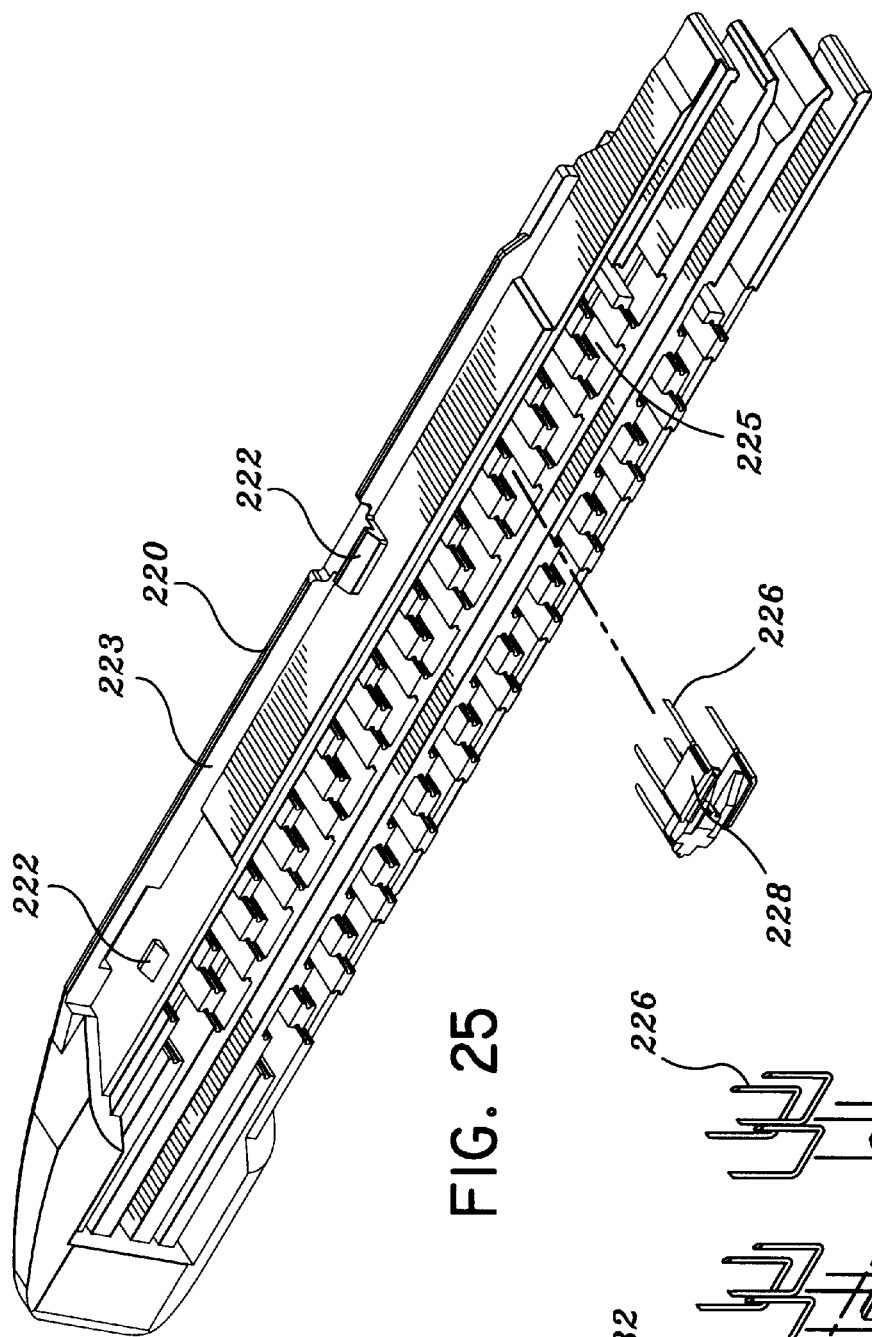
FIG. 25 is a bottom perspective view of the staple cartridge shown in FIG. 21.
Figure 26:
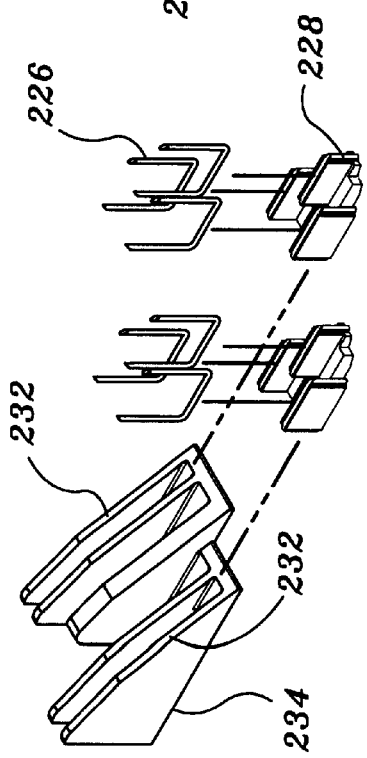
FIG. 26 is an enlarged perspective view of the actuation sled, the pushers and the fasteners shown in FIG. 21.
Figure 31:
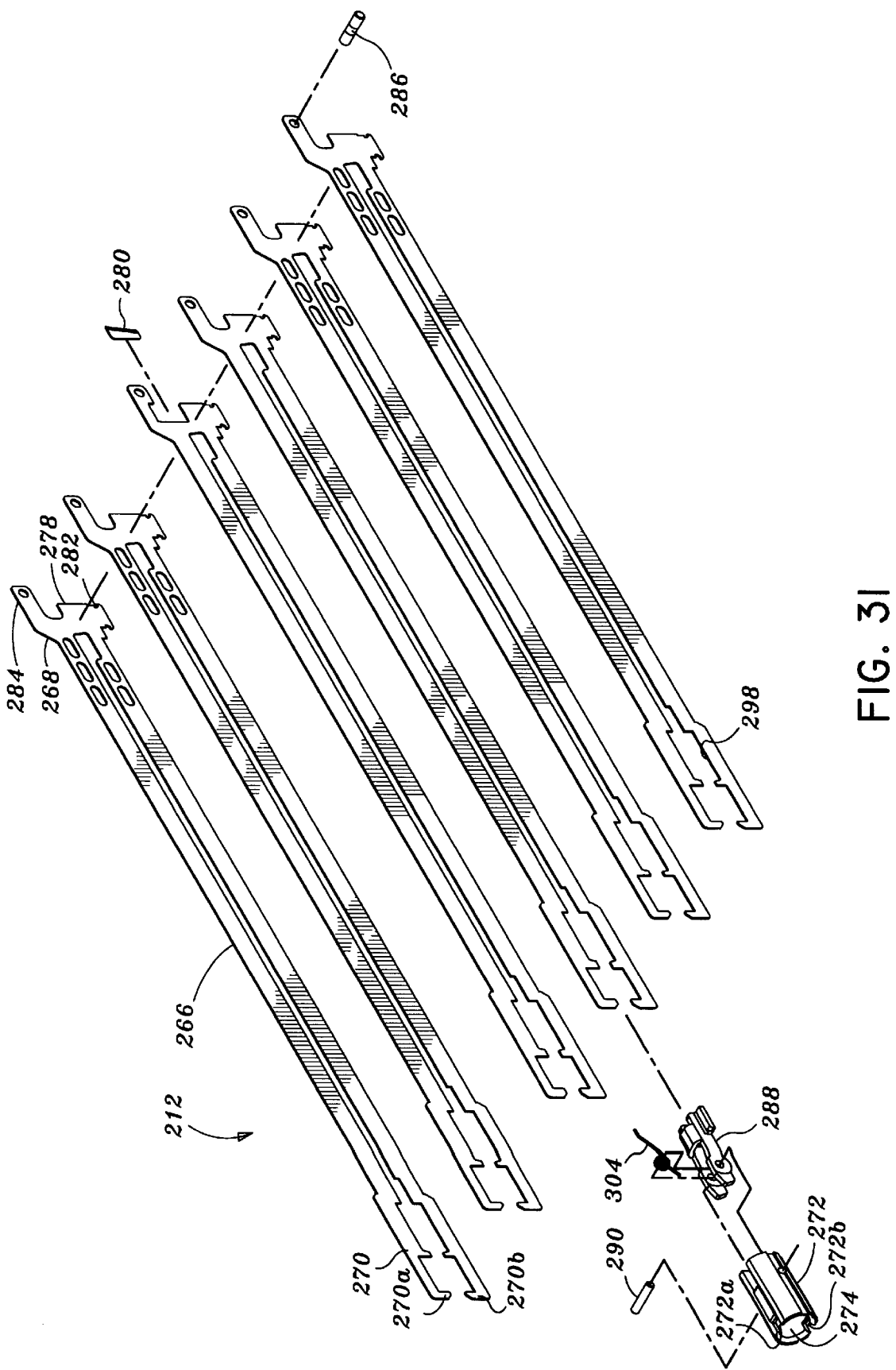
FIG. 31 is a perspective view with parts separated of the axial drive assembly.
Figure 38:
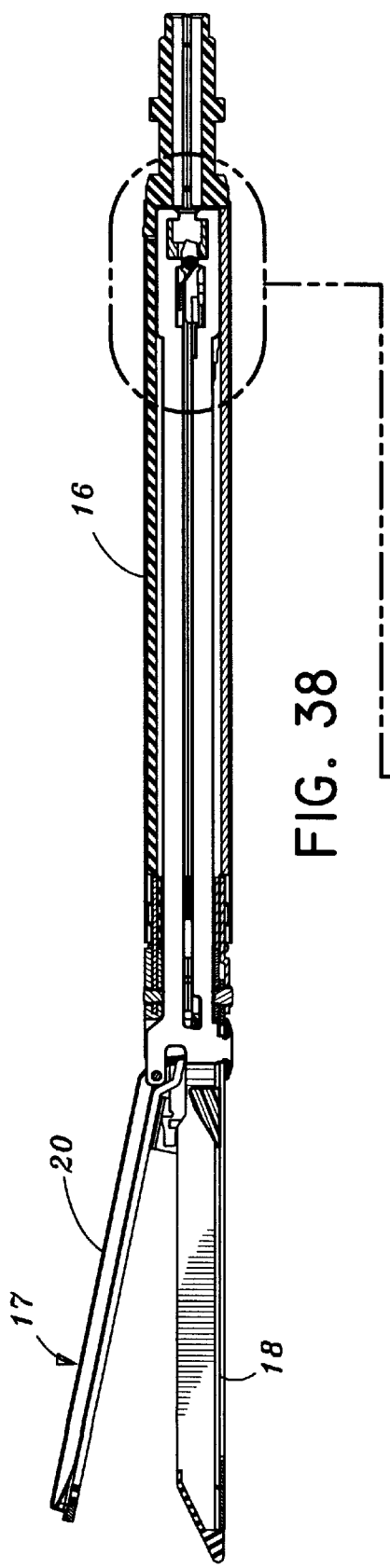
FIG. 38 is a side cross-sectional view of the disposable loading unit shown in FIG. 20.

Referring to FIGS. 19 and 20, disposable loading unit 16 includes a proximal housing portion 200 adapted to releasably engage the distal end of body portion 14 (FIG. 1). A mounting assembly 202 is pivotally secured to the distal end of housing portion 200, and is configured to receive the proximal end of tool assembly 17 such that pivotal movement of mounting assembly 202 about an axis perpendicular to the longitudinal axis of housing portion 200 effects articulation of tool assembly 17.

Referring to FIGS. 21–26, tool assembly 17 preferably includes anvil assembly 20 and cartridge assembly 18. Anvil assembly 20 includes anvil portion 204 having a plurality of staple deforming concavities 206 (FIG. 22) and a cover plate 208 secured to a top surface of anvil portion 204 to define a cavity 210 (FIG. 24) therebetween. Cover plate 208 is provided to prevent pinching of tissue during clamping and firing of stapling apparatus 10. Cavity 210 is dimensioned to receive a distal end of an axial drive assembly 212 (See FIG. 27). A longitudinal slot 214 extends through anvil portion 204 to facilitate passage of retention flange 284 of axial drive assembly 212 into the anvil cavity 210. A camming surface 209 formed on anvil portion 204 is positioned to engage axial drive assembly 212 to facilitate clamping of tissue 198. A pair of pivot members 211 formed on anvil portion 204 are positioned within slots 213 formed in carrier 216 to guide the anvil portion between the open and clamped positions. A pair of stabilizing members 215 engage a respective shoulder 217 formed on carrier 216 to prevent anvil portion 204 from sliding axially relative to staple cartridge 220 as camming surface 209 is deformed.

Cartridge assembly 18 includes a carrier 216 which defines an elongated support channel 218. Elongated support channel 218 is dimensioned and configured to receive a staple cartridge 220. Corresponding tabs 222 and slots 224 formed along staple cartridge 220 and elongated support channel 218 function to retain staple cartridge 220 within support channel 218. A pair of support struts 223 formed on staple cartridge 220 are positioned to rest on side walls of carrier 216 to further stabilize staple cartridge 220 within support channel 218.

Staple cartridge 220 includes retention slots 225 for receiving a plurality of fasteners 226 and pushers 228. A plurality of spaced apart longitudinal slots 230 extend through staple cartridge 220 to accommodate upstanding cam wedges 232 of actuation sled 234. A central longitudinal slot 282 extends along the length of staple cartridge 220 to facilitate passage of a knife blade 280. During operation of surgical stapler 10, actuation sled 234 translates through longitudinal slots 230 of staple cartridge 220 to advance cam wedges 232 into sequential contact with pushers 228, to cause pushers 228 to translate vertically within slots 224 and urge fasteners 226 from slots 224 into the staple deforming cavities 206 of anvil assembly 20.

Referring to FIGS. 27 and 28, mounting assembly 202 includes upper and lower mounting portions 236 and 238. Each mounting portion includes a threaded bore 240 on each side thereof dimensioned to receive threaded bolts 242 (See FIG. 21) for securing the proximal end of carrier 216 thereto. A pair of centrally located pivot members 244 (See FIG. 21) extends between upper and lower mounting portions via a pair of coupling members 246 which engage the distal end of housing portion 200. Coupling members 246 each include an interlocking proximal portion 248 configured to be received in grooves 250 formed in the proximal end of housing portion 200 to retain mounting assembly 202 and housing portion 200 in a longitudinally fixed position in relation thereto.

Housing portion 200 of disposable loading unit 16 includes an upper housing half 250 and a lower housing half 252 contained within an outer casing 251. The proximal end of housing half 250 includes engagement nubs 254 for releasably engaging elongated body 14 and an insertion tip 193. Nubs 254 form a bayonet type coupling with the distal end of body 14 which will be discussed in further detail below. Housing halves 250 and 252 define a channel 253 for slidably receiving axial drive assembly 212. A second articulation link 256 is dimensioned to be slidably positioned within a slot 258 formed between housing halves 250 and 252. A pair of blow out plates 254 are positioned adjacent the distal end of housing portion 200 adjacent the distal end of axial drive assembly 212 to prevent outward bulging of drive assembly 212 during articulation of tool assembly 17.

Referring to FIGS. 29–30, second articulation link 256 includes at least one elongated metallic plate. Preferably, two or more metallic plates are stacked to form link 256. The proximal end of articulation link 256 includes a hook portion 258 configured to engage first articulation link 123 (See FIG. 9) and the distal end includes a loop 260 dimensioned to engage a projection 262 formed on mounting assembly 202. Projection 262 is laterally offset from pivot pin 244 such that linear movement of second articulation link 256 causes mounting assembly 202 to pivot about pivot pins 244 to articulate tool assembly 17.

Referring also to FIGS. 31–34, axial drive assembly 212 includes an elongated drive beam 266 including a distal working head 268 and a proximal engagement section 270. Drive beam 266 may be constructed from a single sheet of material or, preferably, multiple stacked sheets. Engagement section 270 includes a pair of engagement fingers 270a and 270b which are dimensioned and configured to mountingly engage a pair of corresponding retention slots 272a and 272b formed in drive member 272. Drive member 272 includes a proximal porthole 274 configured to receive the distal end 276 of control rod 52 (See FIG. 35) when the proximal end of disposable loading unit 16 is engaged with elongated body 14 of surgical stapling, apparatus 10.

The distal end of drive beam 266 is defined by a vertical support strut 278 which supports a knife blade 280, and an abutment surface 283 which engages the central portion of actuation sled 234 during a stapling procedure. Surface 285 at the base of surface 283 is configured to receive a support member 287 slidably positioned along the bottom of the staple cartridge 220. Knife blade 280 is positioned to translate slightly behind actuation sled 234 through a central longitudinal slot 282 in staple cartridge 220 (FIG. 30) to form an incision between rows of stapled body tissue. A retention flange 284 projects distally from vertical strut 278 and supports a cylindrical cam roller 286 at its distal end. Cam roller 286 is dimensioned and configured to engage cam surface 209 on anvil body 204 to clamp anvil portion 204 against body tissue.

Referring also to FIGS. 36–39, a locking device 288 is pivotally secured to drive member 270 about a pivot pin 290. Locking device 288 includes a pair of elongate glides 292 and 294 which define a channel 296. A web 298 joins a portion of the upper surfaces of glides 292 and 294, and is configured and dimensioned to fit within elongated slot 298 formed in drive beam 266 at a position distal of drive member 270. Horizontal cams 300 and 302 extend from glides 292 and 294 respectively, and are accommodated along an inner surface of lower housing half 252. As best shown in FIG. 42, a torsion spring 304 is positioned adjacent drive member 270 and engages horizontal cams 300 and 302 of locking device 288 to normally bias locking device 288 downward toward lower housing half 252 onto ledge 310. Locking device 288 translates through housing portion 200 with axial drive assembly 212. Operation of locking device 288 will be described below.

Sequence of Operation

Referring to FIGS. 40–44, to use stapling instrument 10, a disposable loading unit 16 is first secured to the distal end of elongated body 14. As discussed above, stapling instrument 10 can be used with articulating and non-articulating disposable loading units having linear rows of staples between about 30 mm and about 60 mm. To secure disposable loading unit 16 to elongated body 14, the distal end 276 of control rod 52 is inserted into insertion tip 193 of disposable loading unit 16, and insertion tip 193 is slid longitudinally into the distal end of elongated body 14 in the direction indicated by arrow "A" in FIG. 41 such that hook portion 258 of second articulation link 256 slides within a channel 310 in elongated body 314. Nubs 254 will each be aligned in a respective channel (not shown) in elongated body 14. When hook portion 258 engages the proximal wall 312 of channel 310, disposable loading unit 16 is rotated in the direction indicated by arrow "B" in FIGS. 41-44 to move hook portion 258 of second articulation link 256 into engagement with finger 164 of first articulation link 123. Nubs 254 also forms a bayonet type coupling within annular channel 314 in body 14. During rotation of loading unit 16, nubs 254 engage cam surface 195 (FIG. 41) of block plate 192 to initially move plate 192 in the direction indicated by arrow "C" in FIGS. 41 and 43 to lock engagement member 196 in recess 199 of control rod 52 to prevent longitudinal movement of control rod 52 during attachment of disposable loading unit 16. During the final degree of rotation, nubs 254 disengage from cam surface 195 to allow blocking plate 192 to move in the direction indicated by arrow "D" in FIGS. 42 and 44 from behind engagement member 196 to once again permit longitudinal movement of control rod 52.

Referring to FIGS. 43 and 43a, when insertion tip 193 engages the distal end of sensor tube 176, the disposable loading unit sensing mechanism is actuated, insertion tip 193 engages and moves sensor tube 176 proximally in the direction indicated by arrow "E" in FIG. 43. As discussed above, proximal movement of sensor tube 176 effects proximal movement of sensor cylinder 178 and sensor link 182 in the direction indicated by arrow "E" in FIG. 43a to pivot locking member 83 counter-clockwise, as indicated by arrow "Y" in FIG. 43a, from a non-blocking position to a position blocking movement of actuation shaft 46.

Figure 45:
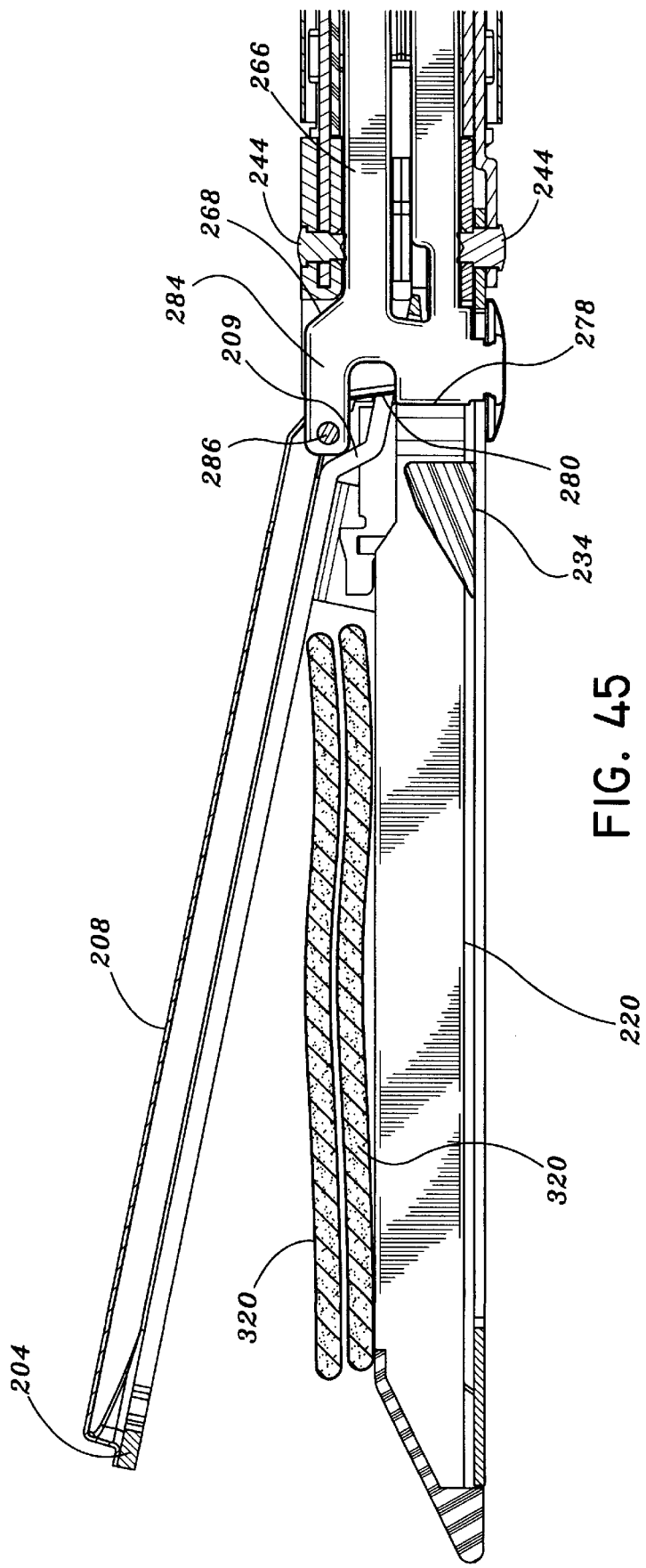
FIG. 45 is a side cross-sectional view of the distal end of the disposable loading unit of FIG. 1 with tissue positioned between the anvil and clamp assemblies.
Figure 46:
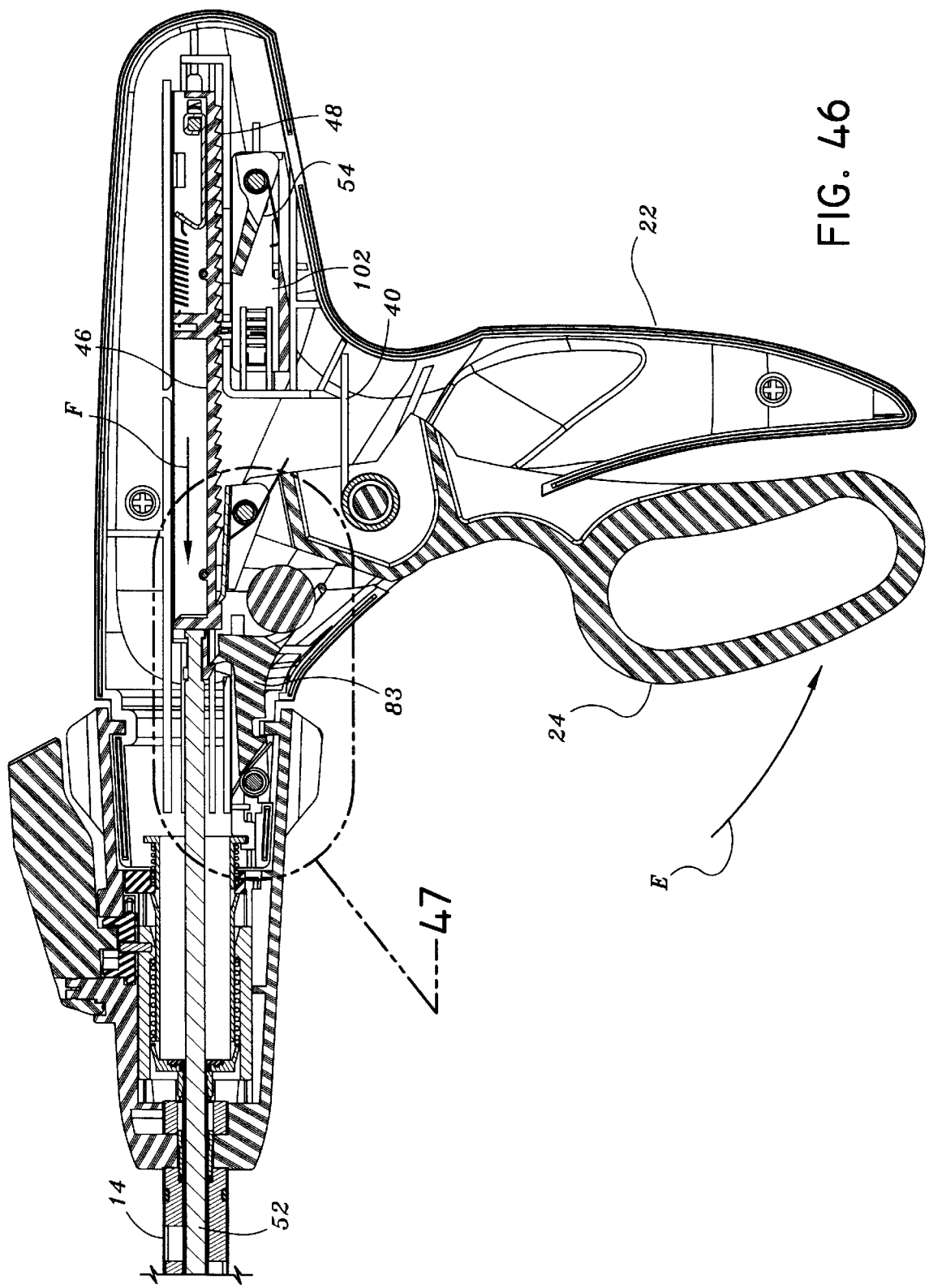
FIG. 46 is a side cross-sectional view of the handle assembly with the movable handle in an actuated position.
Figure 47:
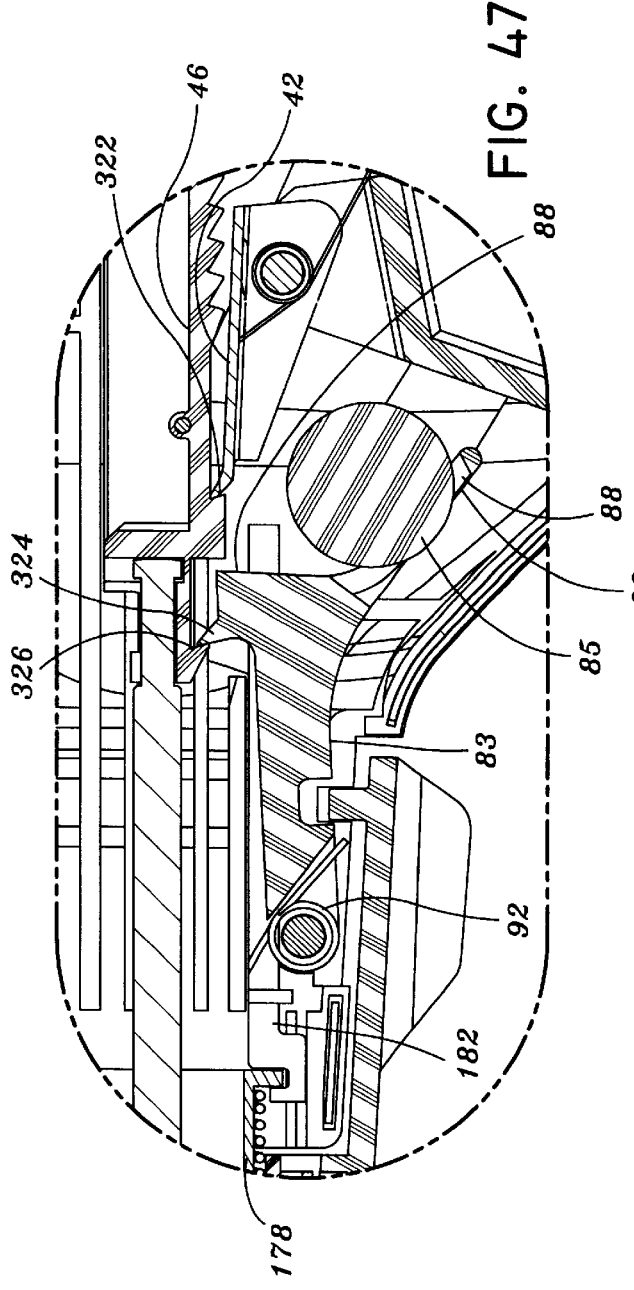
FIG. 47 is an enlarged view of the indicated area of detail shown in FIG. 46.
Figure 48:
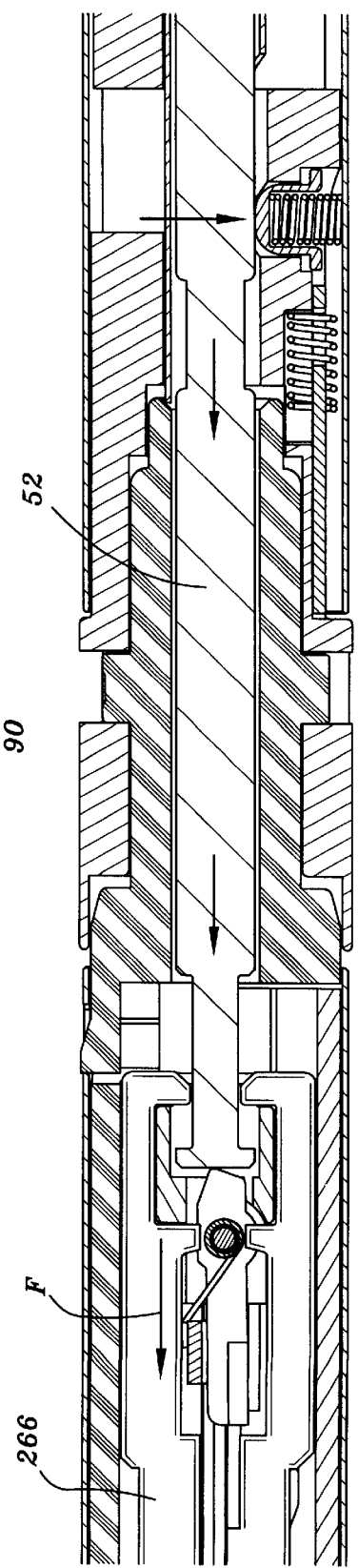
FIG. 48 is a cross-sectional view of the proximal end of the disposable loading unit of FIG. 19 and the distal end of the elongated body of the surgical stapling apparatus shown in FIG. 1 with the control rod in a partially advanced position.
Figure 49:
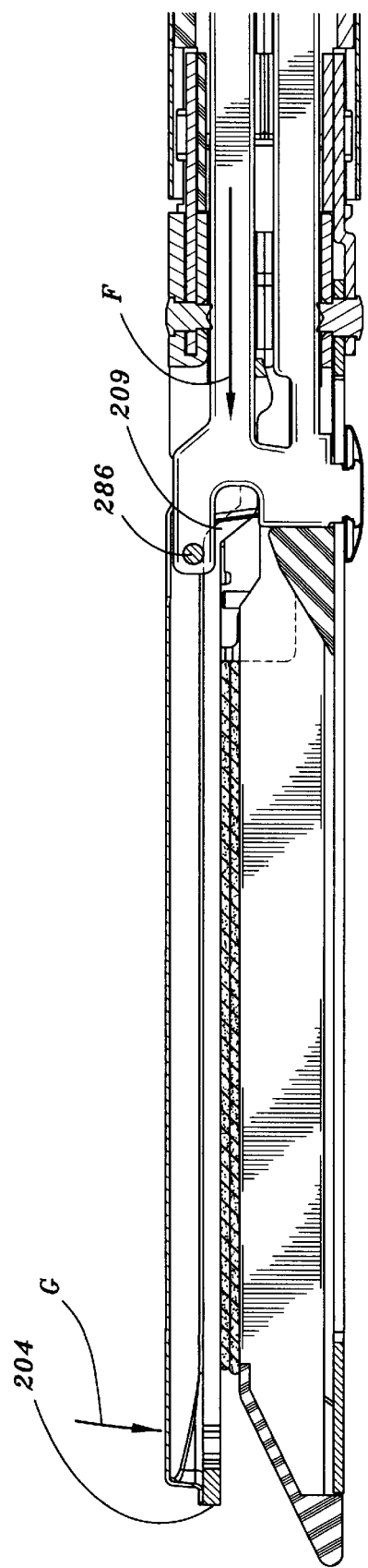
FIG. 49 is a cross-sectional view of the tool assembly of the surgical stapling apparatus shown in FIG. 1 positioned about tissue in the clamped position.

Referring to FIGS. 46–49, with a disposable loading unit attached to stapling instrument 10, tool assembly 17 can be positioned about tissue 320 (FIG. 45). To clamp tissue between anvil assembly 20 and cartridge assembly 18, stationary handle 24 is moved in the direction indicated by arrow "E" in FIG. 46 against the bias of torsion spring 40 to move driving pawl 42 into engagement with shoulder 322 on actuation shaft 46. Engagement between shoulder 322 and driving pawl 42 advances actuation shaft 46 and thus advances control rod 52 distally. Control rod 52 is connected at its distal end to axial drive assembly 212 (FIG. 48), including drive beam 266, such that distal movement of control rod 52 effects distal movement of drive beam 266 in the direction indicated by arrow "F" in FIGS. 48 and 49, moving cam roller 286 into engagement with cam surface 209 on anvil portion 204 to urge anvil portion 204 in the direction indicated by arrow "G" in FIG. 49. It is noted that one complete stroke of movable handle 24 advances actuation shaft 46 approximately 15 mm which is sufficient to clamp tissue during the first stroke but not to fire staples.

As discussed above with respect to the anti-reverse clutch mechanism, during the first (clamping) stroke of movable handle 24, slide plate 102 (FIG. 46) prevents locking pawl 54 from engaging toothed rack 48. To maintain actuation shaft 46 in its longitudinal position after handle 24 is released, an engagement member 324 (FIG. 47) is provided on locking member 83 to engage shoulder 326 on actuation shaft 46 and retain shaft 46 in its longitudinal position (See FIG. 47). Upon release of movable handle 24, drive pawl 42 moves over rack 48 as torsion spring 40 returns handle 24 to a position spaced from stationary handle 22. In this position, driving pawl 42 is urged into engagement with toothed rack 48 to retain actuation shaft 46 in its longitudinal fixed position.

In order to fire staples, movable handle 24 is actuated again, i.e., moved through another stroke. As discussed above, stapling apparatus 10 is capable of receiving disposable loading units having linear rows of staples of between about 30 mm and about 60 mm. Since each stroke of the movable handle 24 preferably advances actuation shaft 46 15 mm, and one stroke is required to clamp tissue, the movable handle must be actuated (n+1) strokes to fire staples, where n is the length of the linear rows of staples in the disposable loading unit attached to stapling instrument 10 divided by 15 mm.

Figure 50:
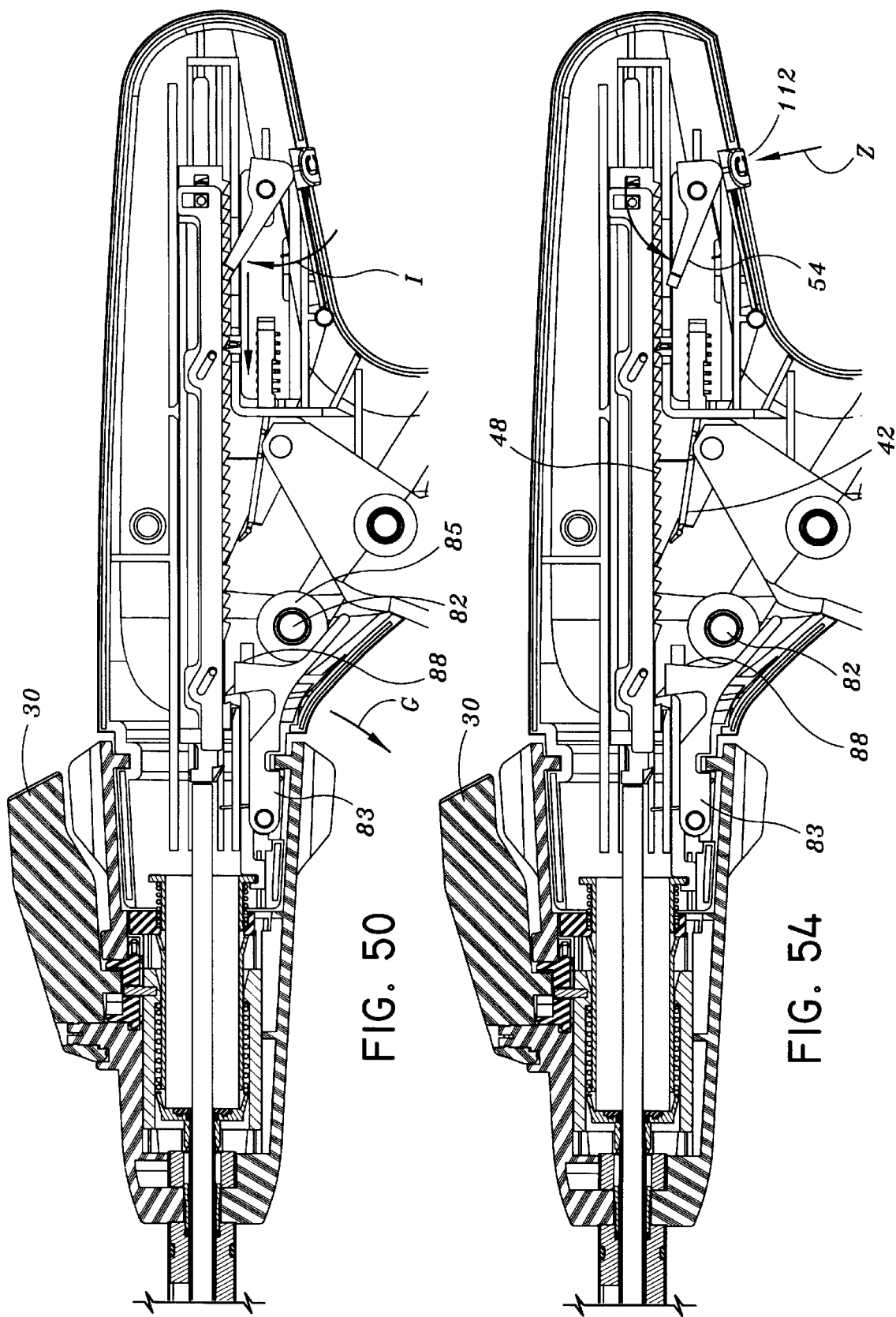
FIG. 50 is a cross-sectional view of the handle assembly of the stapling apparatus of FIG. 1 during the clamping stroke of the apparatus.

Referring to FIG. 50, prior to being able to fire staples, firing lockout assembly 80 (FIG. 4) must be actuated to move locking surface 88 from its blocking position (FIG. 47) to a non-blocking position. This is accomplished by pressing down on plunger 82 to move camming surface 85 into engagement with sidewalls of slot 89 of locking member 83 to pivot locking member 83 in the direction indicated by arrow "G" in FIG. 50 (see also FIG. 5). Thereafter, movable handle 24 may be actuated an appropriate number of strokes to advance actuation shaft 46, and thus control rod 52 and drive beam 266, distally in the direction indicated by arrow "H" in FIGS. 51 and 52 to advance actuation sled 234 through staple cartridge 220 to effect ejection of staples. It is noted that after the first or clamping stroke of movable handle 54 (during the second stroke), slide 102 passes over locking pawl 54 allowing torsion spring 56 to move locking pawl 54 in the direction indicated by arrow "I" in FIG. 50 into engagement with toothed rack 48 to retain actuation shaft 46 in its longitudinal position.

Figure 53:
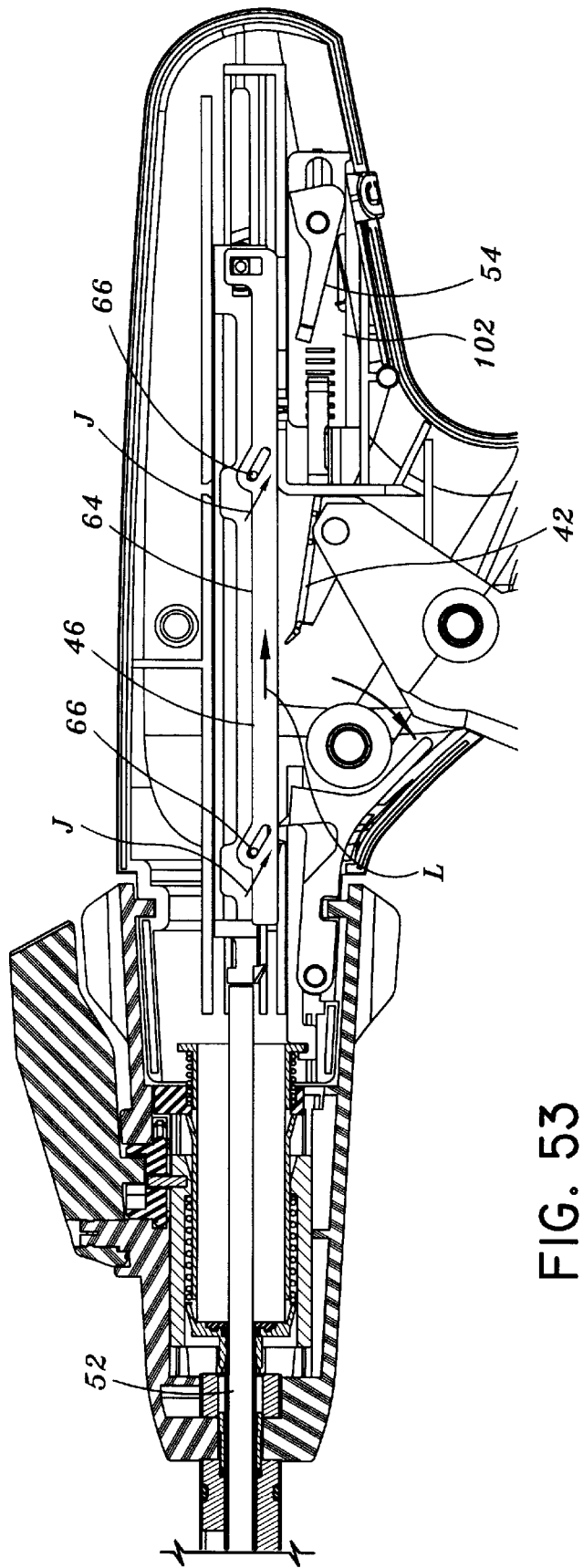
FIG. 53 is a side cross-sectional view of the handle assembly of the apparatus during retraction of the actuation shaft.

Referring to FIG. 53, to retract actuation shaft 46 and thus control rod 52 and drive member 266 after firing staples, retraction knobs 32 (see FIG. 1) are pulled proximally causing pins 66 to move release plate 64 in the direction indicated by arrow "J" in FIG. 53 over teeth 48 to disengage drive pawl 42 from engagement with teeth 48. As discussed above, with respect to the anti-reverse clutch mechanism, locking pawl 54 is urged by slide plate 102 out of engagement with toothed rack 48 (not shown) to permit actuation shaft 46 to be moved proximally, in the direction indicated by arrow "L", after drive pawl 42 is disengaged from teeth 48.

Referring to FIG. 54, in order to retract actuation shaft 46 prior to firing stapling apparatus, i.e., when locking pawl is currently engaged with toothed racked 48, emergency return button 112 is pushed in the direction indicated by arrow "Z" in FIG. 54 to disengage locking pawl 54 from toothed rack 48. Retraction knobs 32 (FIG. 1) must also be concurrently pulled rearwardly, as discussed above, to release drive pawl 42 from rack 48.

Figure 55:
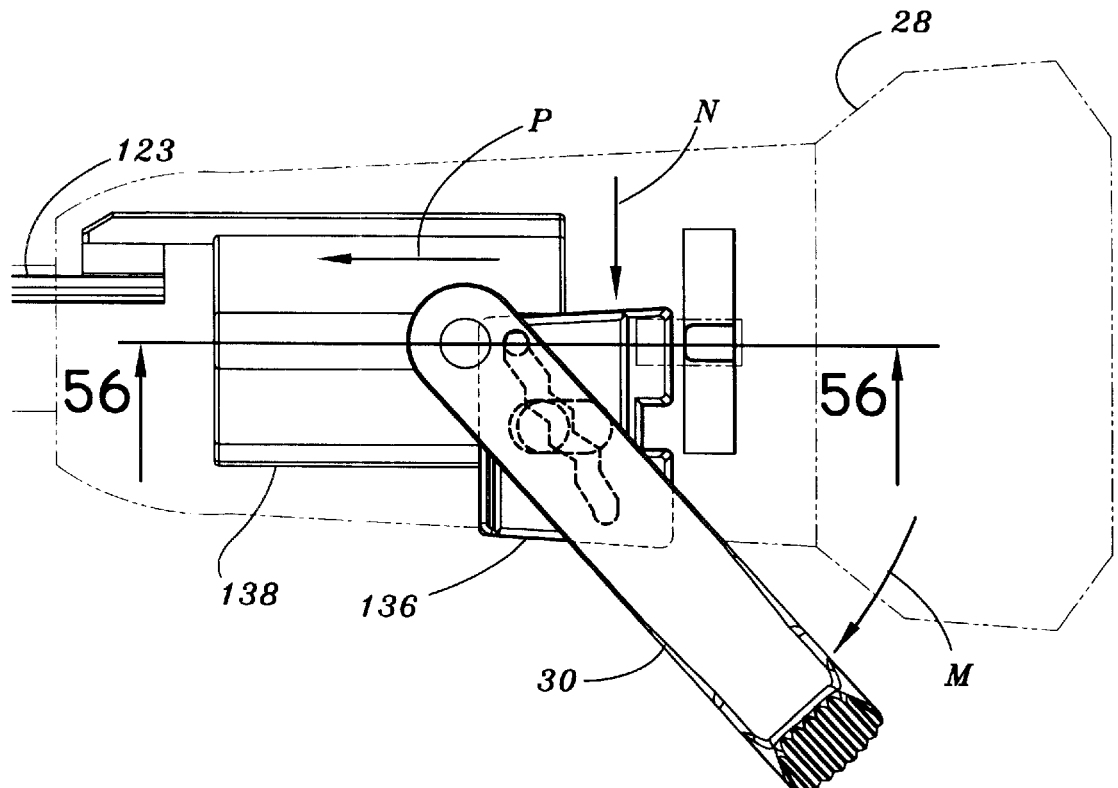
FIG. 55 is a top view of the articulation mechanism of the surgical stapling apparatus.
Figure 56:
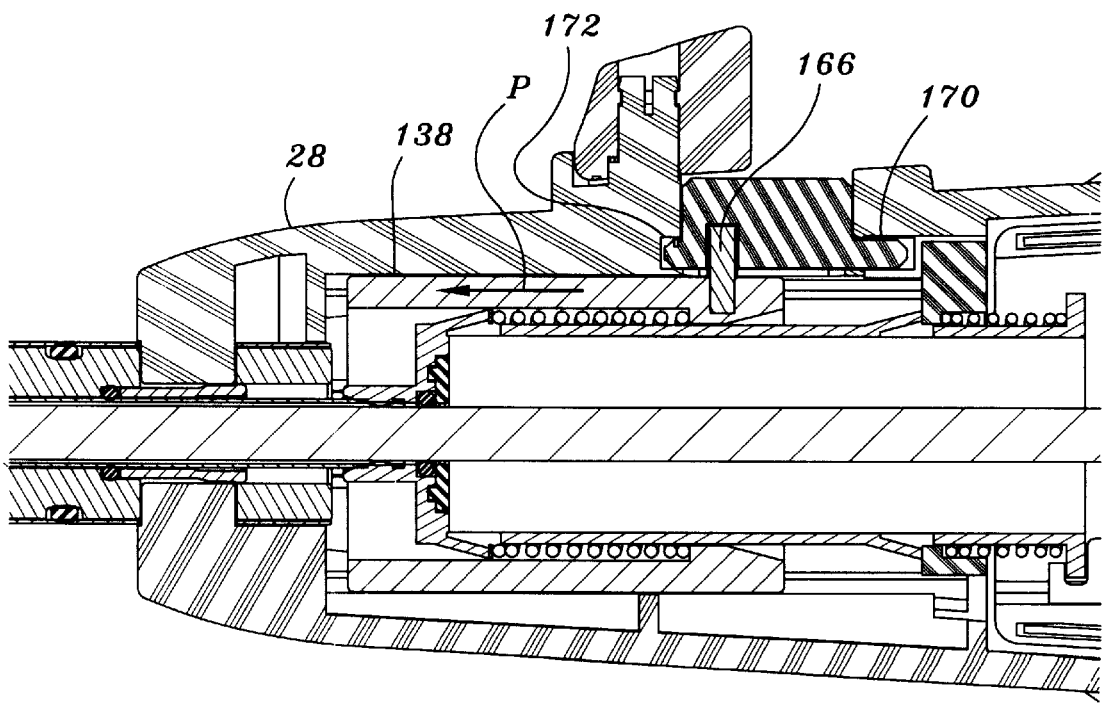
FIG. 56 is a side cross-sectional view of the articulation mechanism and rotation member of the surgical stapling apparatus shown in FIG. 1.
Figure 57:
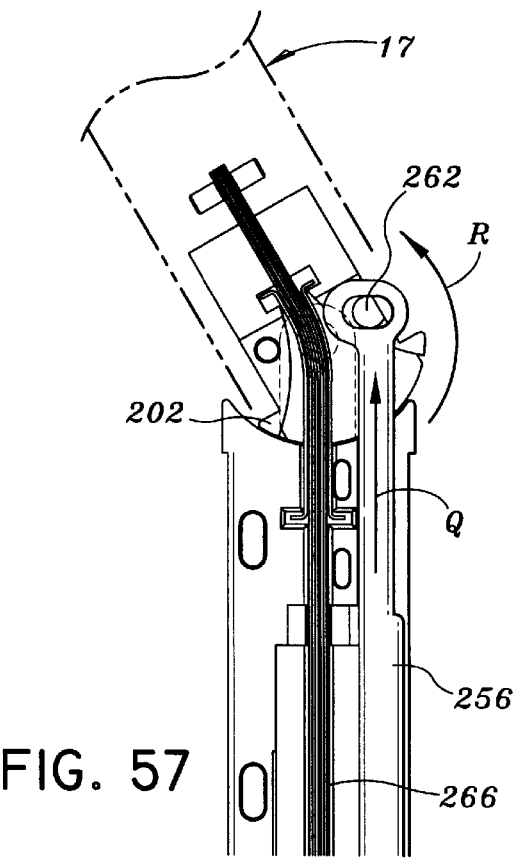
FIG. 57 is a top view of the distal end of the elongated body, the mounting assembly, and the proximal end of the tool assembly during articulation of the stapling apparatus.

Referring to FIGS. 55–61, when an articulating disposable loading unit is secured to elongated body 14 and articulation lever 30 is pivoted in the direction indicated by arrow "M" in FIG. 55, cam member 136 is moved transversely by projection 142 (FIG. 10) in the direction indicated by arrow "N" between flanges 170 and 172 of rotation knob 28. Since translation member 138 is prevented from rotating by ridges 156 (FIG. 13), pin 166, which is fixedly secured to translation member 138, is forced to move along stepped cam surface 148. Movement of pin 166 causes corresponding movement of translation member 138 in the direction indicated by arrow "P" in FIGS. 55 and 56 to advance first articulation link 123 in the distal direction. The distal end of first articulation link 123 engages the proximal end of second articulation link 256 (FIG. 42) which is connected to projection 262 on mounting assembly 202 to advance second link 256 in the direction indicated by arrow "Q" in FIG. 57. Projection 262 is laterally offset from pivot members 244, such that distal advancement of second articulation link 256 causes mounting assembly 202 and thus tool assembly 17 to pivot in the direction indicated by arrow "R" in FIGS. 57 and 58. Note in FIG. 59 that rotation member 28 can be rotated to rotate elongated body 14 about its longitudinal axis while tool assembly 17 is articulated.

Figure 60:
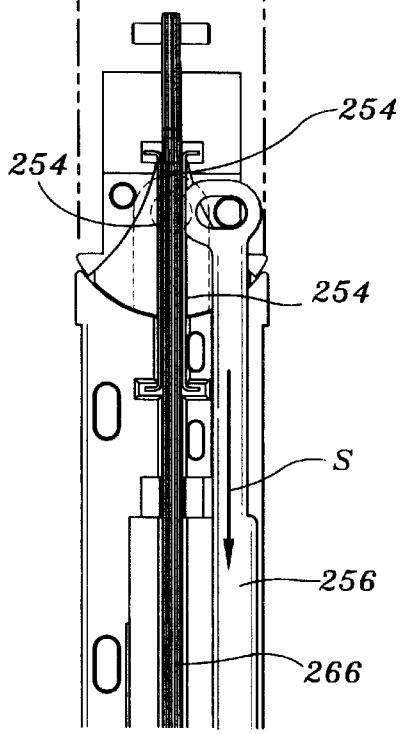
FIG. 60 is a top view of the distal end of the disposable loading unit immediately prior to articulation.
Figure 61:
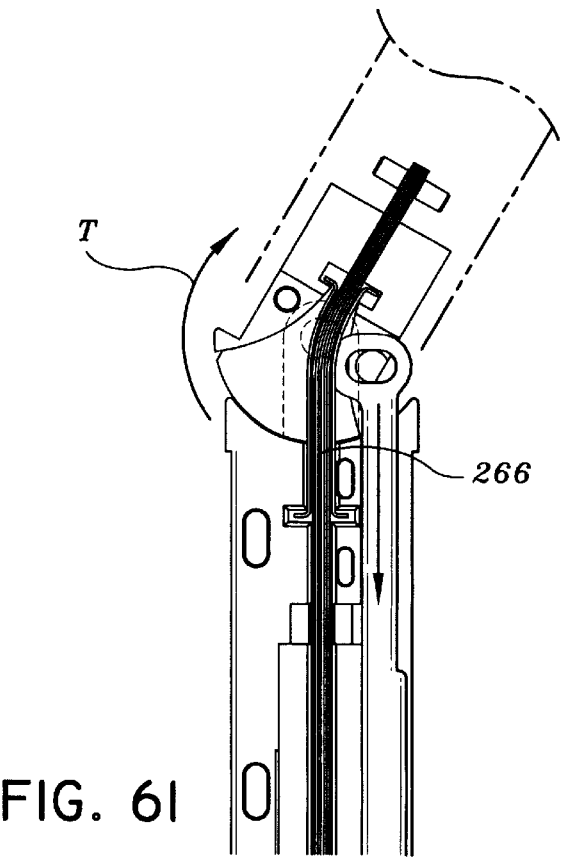
FIG. 61 is a top view of the distal end of the elongated body, the mounting assembly, and the proximal end of the tool assembly during articulation of the stapling apparatus.

FIGS. 60–61 illustrate articulation of tool assembly 17 in the opposite direction to that described above. When second articulation link 256 is retracted by rotating articulation lever 30 in a counter-clockwise direction (not shown) as viewed in FIG. 55, pin 66 is forced to move proximally along stepped camming surface 148, moving translation member 138 and first articulation link 123 proximally. Movement of first articulation link 123 proximally, causes second articulation link 256 to move proximally as indicated by arrow "S" in FIG. 58, to rotate tool assembly 17 in a clockwise direction, as indicated by arrow "T" in FIG. 61.

Referring to FIG. 12, movement of pin 166 (FIG. 9) between adjacent step portions 340 causes tool assembly 17 to articulate 22.5 degrees. Camming surface 148 includes five step portions 340. The third step portion corresponds to the non-articulated tool assembly position, whereas the first and the fifth step portions correspond to articulation of tool assembly 17 to forty-five degrees. Each step portion is flat to retain articulation lever 30 in a fixed position when pin 166 is engaged therewith.

Figure 39:
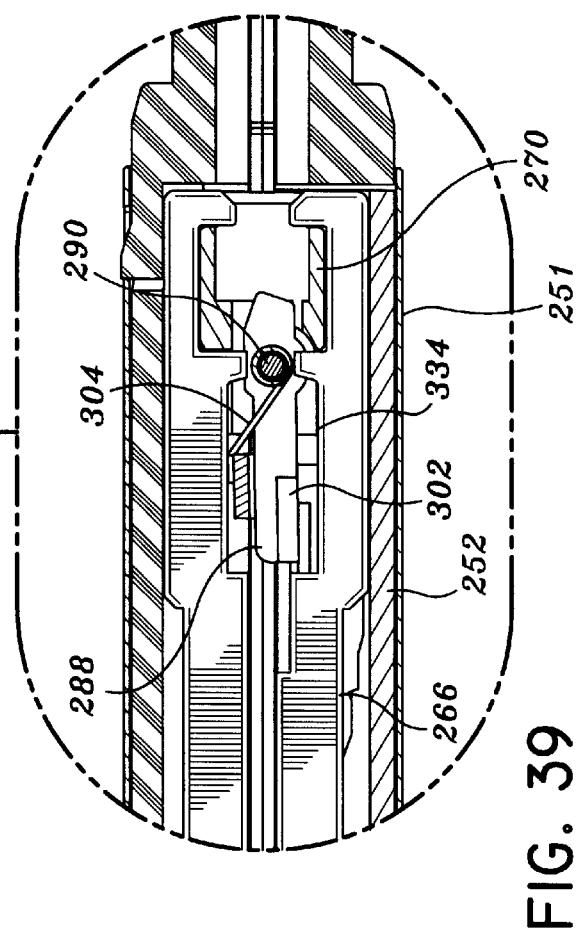
FIG. 39 is an enlarged view of the indicated area of detail shown in FIG. 38.

Referring now to FIGS. 37, 39, 62 and 63, the sequence of lockout operation will be described in detail. In FIG. 39, lockout device 288 is shown in its prefired position with horizontal cams 300 and 302 resting on top of projections 330 formed in the sidewalls of lower housing half 252 (FIG. 37). In this position, locking device 288 is held up out of alignment with projection 332 formed in the bottom surface of lower housing half 252, and web 298 is in longitudinal juxtaposition with shelf 334 defined in drive beam 266. This configuration permits the anvil 20 (FIG. 38) to be opened and repositioned onto the tissue to be stapled until the surgeon is satisfied with the position without activating locking device 288 to disable the disposable loading unit 16.

Figure 62:
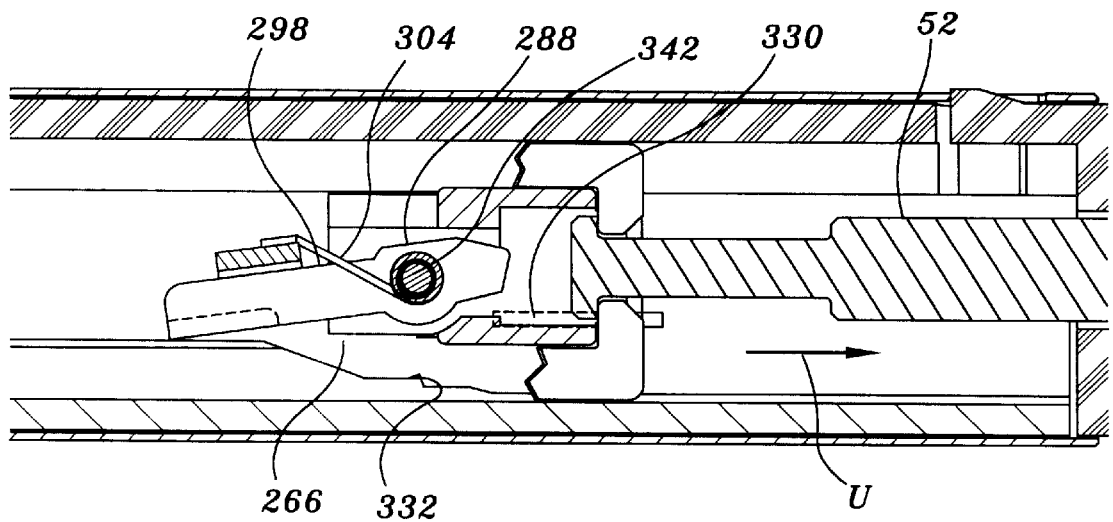
FIG. 62 is a partial cross-sectional view of a portion of the disposable loading unit during retraction of the locking device.
Figure 63:
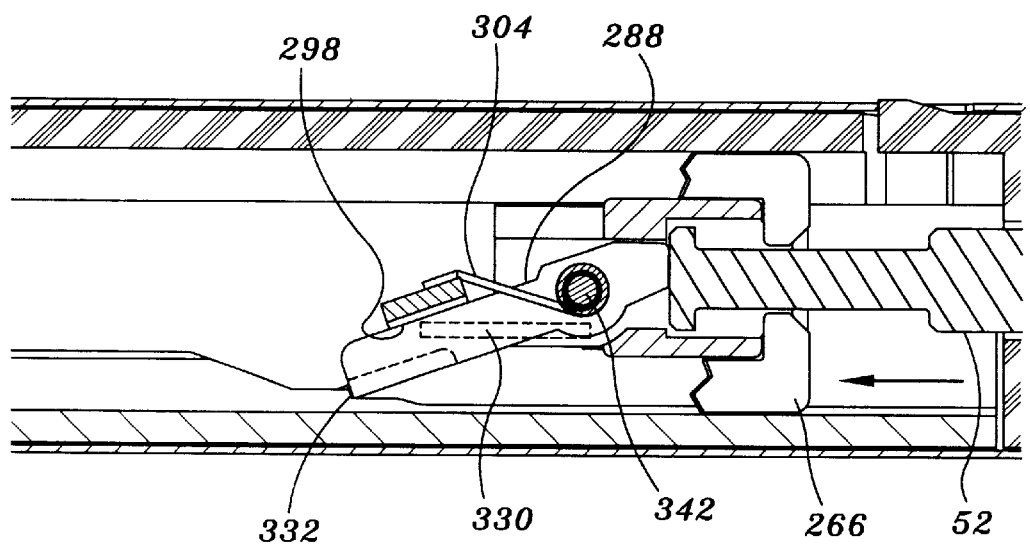
FIG. 63 is a partial cross-sectional view of a portion of the disposable loading unit with the locking device in the locked position.

As shown in FIG. 62, upon distal movement of drive beam 266, locking device 288 rides off of projections 330 (not shown) and is biased into engagement with base lower housing half 252 by spring 304, distal to projection 332. Locking device 288 remains in this configuration throughout firing of the apparatus.

Upon retraction of the drive beam 266 in the direction indicated by arrow "U" in FIG. 62, locking device 288 passes under projections 330 and rides over projection 332 until the distalmost portion of locking device 288 is proximal to projection 332. Spring 304 biases locking device 288 into juxtaposed alignment with projection 332, effectively disabling the disposable loading unit. If an attempt is made to reactuate the apparatus, the control rod 52 will abut a proximal end surface of locking device 288 which surface is diagonally sloped to impart a moment about pivot pin 342 such that the distal end of locking device 288 is rotationally urged into contact with projection 332. Continued distal force in the direction indicated by arrow "W" in FIG. 63, will only serve to increase the moment applied to the locking device thus the locking device will abut projection 332 and inhibit distal movement of the control rod 52.

Referring again to FIGS. 41–44, the disabled or locked disposable loading unit can be removed from the distal end of elongated body 14 by rotating disposable loading unit 16 in the direction opposite to the direction indicated by arrow "B" in FIGS. 41, 42 and 44, to disengage hook portion 258 of second articulation link 256 from finger 164 of first articulation link 123, and to disengage nubs 254 from within channel 314 of elongated body 14. After rotation, disposable loading unit 16 can be slid in the direction opposite to that indicated by arrow "A" in FIG. 41 to detach body 14 from disposable loading unit 16. Subsequently, additional articulating and/or non-articulating disposable loading units can be secured to the distal end of elongated body, as described above, to perform additional surgical stapling and/or cutting procedures. As discussed above, each disposable loading unit may include linear rows of staples which vary from about 30 mm to about 60 mm.

It will be understood that various modifications may be made to the embodiments disclosed herein. For example, the stapling apparatus need not apply staples but rather may apply two part fasteners as is known in the art. Further, the length of the linear row of staples or fasteners may be modified to meet the requirements of a particular surgical procedure. Thus, the length of a single stroke of the actuation shaft and/or the length of the linear row of staples and/or fasteners within a disposable loading unit may be varied accordingly. Therefore, the above description should not be construed as limiting, but merely as exemplifications of preferred embodiments. Those skilled in the art will envision other modifications within the scope and spirit of the claims appended thereto.

What is claimed is:

1. A surgical stapling apparatus comprising:
  a) a housing;
  b) a movable handle supported by the housing, the movable handle being movable through an actuation stroke;

c) an elongated body extending distally from the housing and defining a longitudinal axis, the elongated body having a distal end adapted to releasably engage a disposable loading unit;

d) an advancement assembly including an actuation shaft and a driving pawl, the actuation shaft having a toothed rack and being supported at least in part within the housing, the driving pawl being operatively associated with the movable handle and biased into engagement with the rack, wherein during the actuation stroke, the driving pawl is movable to effect longitudinal advancement of the actuation shaft; and e) a retraction mechanism including a release plate operatively associated with the actuation shaft, the release plate being movable relative to the actuation shaft into operative engagement with the driving pawl to disengage the driving pawl from the rack.

2. A surgical stapling apparatus according to claim 1, wherein the retraction mechanism further includes at least one retractor knob positioned externally of the housing, the at least one retractor knob being operatively connected to the release plate and movable to move the release plate into engagement with the driving pawl.

3. A surgical stapling apparatus according to claim 2, wherein the release plate includes at least one cam slot and the actuation shaft has a pin positioned within each cam slot, the release plate being connected to the at least one retractor knob by a coupling rod such that movement of the coupling rod causes the release plate to move relative to the actuation shaft causing the pin to cam the release plate into engagement with the driving pawl.

4. A surgical stapling apparatus according to claim 2, wherein the driving pawl includes a laterally extending wing, the release plate being movable into engagement with the laterally extending wing to disengage the driving pawl from the rack.

5. A surgical stapling apparatus comprising:

a) a housing;

b) a movable handle supported by the housing, the movable handle being movable through an actuation stroke;

c) an elongated body extending distally from the housing and defining a longitudinal axis, the elongated body having a distal end adapted to releasably engage a disposable loading unit;

d) an advancement assembly including an actuation shaft, a driving pawl and a locking pawl, the actuation shaft having a toothed rack and being supported at least in part within the housing, the driving pawl being operatively associated with the movable handle and movable into engagement with the rack to effect longitudinal advancement of the actuation shaft during the actuation stroke, the locking pawl being biased into engagement with the rack to retain the actuation shaft in a longitudinally fixed position; and e) an anti-reverse clutch mechanism including a gear assembly and a slide plate, the gear assembly being positioned to translate movement of the actuation shaft into movement of the slide plate, the slide plate having a cam surface and being movable, in response to longitudinal advancement of the actuation shaft, from a first position in which the cam surface engages the locking pawl to urge the locking pawl out of engagement with the rack to a second position in which the cam surface is spaced from the locking pawl.

6. A surgical stapling apparatus according to claim 5, wherein the gear assembly includes a first gear and a second gear operatively connected to each other, the actuation shaft and the slide plate each having a set of gear teeth, the first gear being positioned to mesh with the actuation shaft gear teeth and the second gear being positioned to mesh with the slide plate gear teeth such that longitudinal advancement of the actuation shaft translates to longitudinal advancement of the slide plate during at least a portion of the longitudinal advancement of the actuation shaft.

7. A surgical stapling apparatus according to claim 6, further including a pin fixedly mounted within the housing, wherein the slide plate includes an elongated slot configured to receive the pin, the pin being positioned to abut ends of the slot to limit longitudinal advancement of the slide plate.

8. A surgical stapling apparatus according to claim 7, wherein the first gear is rotatably mounted on a first shaft and the second gear is rotatably mounted on a second shaft, the first and second shafts being operatively connected to each other by a spring clutch, the spring clutch permitting the first shaft to rotate independently of the second shaft after the pin prevents further longitudinal advancement of the slide plate.

9. A surgical stapling apparatus according to claim 8, wherein the actuation shaft includes first and second sets of gear teeth, the first and second sets of gear teeth of the actuation shaft being positioned to mesh with the first gear during at least a portion of the longitudinal advancement of the actuation shaft, the first set of gear teeth being positioned on the actuation shaft to advance the slide plate longitudinally from a position in which the cam surface engages the locking pawl to a position in which the cam surface is spaced from the locking pawl and the second set of gear teeth being positioned on the actuation shaft to return the slide plate proximally during retraction of the actuation shaft from a position in which the cam surface is spaced from the locking pawl to a position in which the cam surface engages the locking pawl to urge the locking pawl out of engagement from the rack.

* * * * *

UNITED STATES PATENT AND TRADEMARK OFFICE
CERTIFICATE OF CORRECTION

PATENT NO. : 6,330,965 B1  
APPLICATION NO. : 09/680093  
DATED : December 18, 2001  
INVENTOR(S) : Milliman et al.

Page 1 of 1

It is certified that error appears in the above-identified patent and that said Letters Patent is hereby corrected as shown below:

COLUMN 1, LINE 5:

"This application is a divisional of U.S. patent application Ser. No. 09/166,378, filed Oct. 5, 1998, now U.S. Pat. No. 6,079,606, which is a divisional of U.S. patent application Ser. No. 08/935,980, filed Sep. 23, 1997, now U.S. Pat. No. 5,865,361. Both are incorporated herein by reference." should read --This application is a divisional of U.S. Patent Application Ser. No. 09/561,567, filed Apr. 28, 2000, now U.S. Patent No. 6,241,139, which is a divisional of U.S. Patent Application Ser. No. 09/166,378, filed Oct. 5, 1998, now U.S. Patent No. 6,079,606, which is a divisional of U.S. Patent Application Ser. No. 08/935,980, filed Sep. 23, 1997, now U.S. Patent No. 5,865,361, the entire contents of each of which are incorporated herein by reference.--

Signed and Sealed this  
Twenty-sixth Day of April, 2011

David J. Kappos  
*Director of the United States Patent and Trademark Office*